United States Patent
Norrby et al.

(10) Patent No.: US 7,841,720 B2
(45) Date of Patent: Nov. 30, 2010

(54) METHODS OF OBTAINING OPHTHALMIC LENSES PROVIDING THE EYE WITH REDUCED ABERRATIONS

(75) Inventors: Sverker Norrby, Groningen (NL); Pablo Artal, Murcia (ES); Patricia Ann Piers, Groningen (NL); Marrie Van Der Mooren, Engelbert (NL)

(73) Assignee: AMO Groningen B.V., Groningen (NL)

( * ) Notice: Subject to any disclaimer, the term of this patent is extended or adjusted under 35 U.S.C. 154(b) by 173 days.

(21) Appl. No.: 12/175,395

(22) Filed: Jul. 17, 2008

(65) Prior Publication Data
US 2009/0036980 A1 Feb. 5, 2009

Related U.S. Application Data

(60) Continuation of application No. 11/619,098, filed on Jan. 2, 2007, now abandoned, which is a division of application No. 10/606,910, filed on Jun. 26, 2003, now Pat. No. 7,241,311, which is a division of application No. 09/863,546, filed on May 23, 2001, now Pat. No. 6,609,793.

(30) Foreign Application Priority Data

| May 23, 2000 | (SE) | .................................... 0001925 |
| Dec. 22, 2000 | (SE) | .................................... 0004830 |

(51) Int. Cl.
*A61B 3/10* (2006.01)
(52) U.S. Cl. ..................... 351/212; 623/6.11
(58) Field of Classification Search ................. 351/205, 351/211, 212, 216, 219, 246, 247; 623/6.11, 623/6.23, 6.27; 359/565
See application file for complete search history.

(56) References Cited

U.S. PATENT DOCUMENTS

| 3,722,986 A | 3/1973 | Tagnon |
| 3,950,082 A | 4/1976 | Volk |
| 3,960,442 A | 6/1976 | Davis et al. |
| 4,055,379 A | 10/1977 | Winthrop |
| 4,190,621 A | 2/1980 | Greshes |
| 4,268,133 A | 5/1981 | Fischer et al. |

(Continued)

FOREIGN PATENT DOCUMENTS

EP 949529 A2 10/1999

(Continued)

OTHER PUBLICATIONS

Database PubMed "Online!" NCBI; Seitz et al "Corneal Topography," Database Accession No. 10170448 XP002177903 (1997).

(Continued)

*Primary Examiner*—George Manuel

(57) ABSTRACT

The present invention discloses methods of obtaining ophthalmic lens capable of reducing the aberrations of the eye comprising the steps of characterizing at least one corneal surface as a mathematical model, calculating the resulting aberrations of said corneal surface(s) by employing said mathematical model, selecting the optical power of the intraocular lens. From this information, an ophthalmic lens is modeled so a wavefront arriving from an optical system comprising said lens and corneal model obtains reduced aberrations in the eye. Also disclosed are ophthalmic lenses as obtained by the methods which are capable reducing aberrations of the eye.

45 Claims, 11 Drawing Sheets

U.S. PATENT DOCUMENTS

| | | | |
|---|---|---|---|
| 4,310,225 A | 1/1982 | Davis |
| 4,322,135 A | 3/1982 | Freeman |
| 4,504,982 A | 3/1985 | Burk |
| 4,512,039 A | 4/1985 | Lieberman |
| 4,522,194 A | 6/1985 | Normann |
| 4,580,882 A | 4/1986 | Nuchman et al. |
| 4,640,595 A | 2/1987 | Volk |
| 4,710,193 A | 12/1987 | Volk |
| 4,859,261 A | 8/1989 | Ace |
| 5,009,497 A | 4/1991 | Cohen |
| 5,050,981 A | 9/1991 | Roffman |
| 5,123,921 A | 6/1992 | Werblin et al. |
| 5,125,728 A | 6/1992 | Newman et al. |
| 5,125,729 A | 6/1992 | Mercure |
| 5,236,970 A | 8/1993 | Christ et al. |
| 5,282,852 A | 2/1994 | Capetan et al. |
| 5,444,106 A | 8/1995 | Zhou et al. |
| 5,455,641 A | 10/1995 | Hahne et al. |
| 5,507,806 A | 4/1996 | Blake |
| 5,570,143 A | 10/1996 | Newman |
| 5,652,638 A | 7/1997 | Roffman et al. |
| 5,715,090 A * | 2/1998 | Meyers ........................ 359/565 |
| 5,754,270 A | 5/1998 | Rehse et al. |
| 5,757,458 A | 5/1998 | Miller et al. |
| 5,760,871 A | 6/1998 | Kosoburd et al. |
| 5,766,016 A | 6/1998 | Sinclair et al. |
| 5,771,088 A | 6/1998 | Perrott |
| 5,777,719 A | 7/1998 | Williams et al. |
| 5,786,883 A | 7/1998 | Miller et al. |
| 5,796,462 A | 8/1998 | Roffman et al. |
| 5,800,532 A | 9/1998 | Lieberman |
| 5,805,260 A | 9/1998 | Roffman et al. |
| 5,817,130 A | 10/1998 | Cox et al. |
| 5,824,074 A | 10/1998 | Koch |
| 5,847,802 A | 12/1998 | Menezes et al. |
| 5,953,098 A | 9/1999 | Lieberman et al. |
| 5,963,299 A | 10/1999 | Reyburn |
| 5,968,095 A | 10/1999 | Norrby |
| 6,007,747 A | 12/1999 | Blake et al. |
| 6,050,687 A | 4/2000 | Bille et al. |
| 6,056,401 A | 5/2000 | Shirayanagi |
| 6,079,826 A | 6/2000 | Appleton et al. |
| 6,082,856 A | 7/2000 | Dunn et al. |
| 6,086,204 A | 7/2000 | Magnante |
| 6,089,710 A | 7/2000 | Zeidler |
| 6,095,651 A | 8/2000 | Williams et al. |
| 6,106,118 A | 8/2000 | Menezes et al. |
| 6,106,553 A | 8/2000 | Feingold |
| 6,116,734 A | 9/2000 | Pedrono et al. |
| 6,142,625 A | 11/2000 | Sawano et al. |
| 6,176,578 B1 | 1/2001 | Clutterbuck et al. |
| 6,176,579 B1 | 1/2001 | Mandell |
| 6,197,058 B1 | 3/2001 | Portney |
| 6,203,156 B1 | 3/2001 | Wu et al. |
| 6,213,603 B1 | 4/2001 | Altheimer et al. |
| 6,215,096 B1 | 4/2001 | Von Wallfeld et al. |
| 6,224,211 B1 | 5/2001 | Gordon |
| 6,260,966 B1 | 7/2001 | Sawano et al. |
| 6,276,994 B1 | 8/2001 | Yoshida et al. |
| 6,280,470 B1 | 8/2001 | Peyman |
| 6,305,802 B1 | 10/2001 | Roffman et al. |
| 6,361,166 B1 | 3/2002 | Perrott et al. |
| 6,382,789 B1 | 5/2002 | Baudart et al. |
| 6,390,623 B1 | 5/2002 | Kokonaski et al. |
| 6,413,276 B1 | 7/2002 | Werblin |
| 6,413,277 B1 | 7/2002 | Neuhann |
| 6,416,550 B2 | 7/2002 | Freeman |
| 6,419,359 B2 | 7/2002 | Edwards |
| 6,428,573 B2 | 8/2002 | Barnett |
| 6,454,409 B1 | 9/2002 | Lorenz et al. |
| 6,457,826 B1 | 10/2002 | Lett |
| 6,491,721 B2 | 12/2002 | Freeman et al. |
| 6,533,416 B1 | 3/2003 | Fermigier et al. |
| 6,582,076 B1 | 6/2003 | Roffman et al. |
| 6,595,639 B1 | 7/2003 | Ho et al. |
| 6,609,793 B2 | 8/2003 | Norrby et al. |
| 6,616,692 B1 | 9/2003 | Glick et al. |
| 6,638,305 B2 | 10/2003 | Laguette |
| 6,655,803 B1 | 12/2003 | Rubinstein et al. |
| 6,663,240 B2 | 12/2003 | Patel |
| 6,709,105 B2 | 3/2004 | Menezes |
| 7,137,702 B2 | 11/2006 | Piers et al. |
| 7,241,311 B2 | 7/2007 | Norrby et al. |
| 7,303,281 B2 | 12/2007 | Wakil et al. |
| 7,350,916 B2 | 4/2008 | Hong et al. |
| 2002/0105617 A1 | 8/2002 | Norrby et al. |
| 2002/0122153 A1 | 9/2002 | Piers et al. |
| 2002/0154271 A1 * | 10/2002 | Donitzky et al. ............. 351/212 |
| 2002/0173846 A1 | 11/2002 | Blake et al. |
| 2002/0196410 A1 | 12/2002 | Menezes |
| 2003/0014107 A1 | 1/2003 | Reynard |
| 2003/0033011 A1 | 2/2003 | Singer et al. |
| 2003/0060880 A1 | 3/2003 | Feingold |
| 2003/0090623 A1 | 5/2003 | Rubinstein et al. |
| 2006/0238702 A1 | 10/2006 | Glick et al. |

FOREIGN PATENT DOCUMENTS

| | | |
|---|---|---|
| EP | 964285 A1 | 12/1999 |
| EP | 1262814 A2 | 12/2002 |
| JP | 63240846 A2 | 10/1988 |
| JP | 4110812 A2 | 4/1992 |
| JP | 4126144 A2 | 4/1992 |
| WO | WO-9303409 A1 | 2/1993 |
| WO | WO-9531156 A1 | 11/1995 |
| WO | WO9831299 | 7/1998 |

OTHER PUBLICATIONS

Artal et al., "Contributions of the cornea and the lens to the aberrations of the human eye," Optics Letters, 1998, 23 (21), 1713-1715.

Atchinson, "Design of aspheric intraocular lens," Ophthal Physiol Opt, 1991, 11, 137-146.

Atchinson, "Optical design of intraocular lenses," I On-axis performance Optometry & Vision Science, 1989, 66 (8), 492-506.

Atchinson, "Optical design of intraocular lenses," II On-axis performance Optometry & Vision Science, 1989, 66 (9), 579-590.

Atchinson, "Optical design of intraocular lenses," III On-axis performance Optometry & Vision Science, 1989, 66 (10), 671-681.

Atchinson, "Refractive errors induced by displacement of intraocular lenses within the pseudophakic eye," Optometry & Vision Science, 1989, 66 (3), 146-152.

Atchinson, "Third-order aberrations of pseudophakic eyes," Ophthal. Physiol. Opt., 1989, 9, 205-211.

Bonnet et al., "New method of topographical ophthalmometry-its theoretical and clinical applications," American Journal of Optometry and Archives of American Academy of Optometry, 1962, 39 (5), 227-251.

El Hage et al., "Contribution of the crystalline lens to the spherical aberration of the eye," Journal of the Optical Society of America, 1973, 63 (2), 205-211.

Glasser A. et al., "Presbyopia and the optical changes in the human crystalline lens with age," Vision Res, 1998, 38 (2), 209-229.

Greivenkamp et al., "Visual acuity modeling using optical raytracing of schematic eyes," American Journal of Ophthalmology, 1995, 120 (2), 227-240.

Guillon et al., "Corneal topography: a clinical model," Ophthal. Physiol. Opt, 1986, 6 (1), 47-56.

Guirao Antonio et al., "Corneal wave aberration from videokeratography: accuracy and limitations of the procedure," Journal of Optical Society of America, 2000, 17 (6), 955-965.

Iovs, 1999, 40 (4), S535.

Kiely et al., "The mean shape of the human cornea," Optica ACTA, 1982, 29 (8), 1027-1040.

Lang J. et al., "Objective measurement of wave aberrations of the human eye with the use of a Hartmann-Shack wave-front sensor," J Opt Soc Am A Opt Image Sci Vis, 1994, 11 (7), 1949-1957.

Lindsay et al., "Descriptors of corneal shape," Optometry and Vision Science, 1998, 75 (2), 156-158.

Lotmar, "Theoretical eye model with aspherics," Journal of the Optical Society of America, 1971, 61 (11), 1522-1529.

Malacara et al., "Wavefront fitting with discrete orthogonal polynomials in a unit radius circle," Optical Engineering, 1990, 29 (6), 672-675.

Mandell et al., "Mathematical model of the corneal contour," School of Optometry, University of California, 183-197.

Oshika et al., "Changes in corneal wavefront aberrations with aging," Investigative Ophthalmology & Visual Science, 1999, 40 (7), 1351-1355.

Patel, S. et al, Refractive & Corneal Surgery, pp. 172-181, 1993, vol. 9.

Schwiegerlind et al., "Representation of videokeratoscopic height data with Zernike polynomials," Journal of the Optical Society of America, 1995, 12 (10), 2105-2113.

Smith et al., "The spherical aberration of intra-ocular lenses," Ophthal. Physiol, 1988, 8, 287-294.

Smith G. et al., "The spherical aberration of the crystalline lens of the human eye," Vision Res., 2001, 41 (2), 235-243.

Townsley, "New Knowledge of the corneal contour," 38-43.

Wang et al., "Wave-front interpretation with Zernike polynomials," Applied Optics, 1980, 19 (9), 1510-1518.

* cited by examiner

METHODS OF OBTAINING OPHTHALMIC LENSES PROVIDING THE EYE WITH REDUCED ABERRATIONS

RELATED APPLICATIONS

The present application is a continuation application of U.S. Ser. No. 11/619,098, filed Jan. 2, 2007, which is a divisional application of U.S. Ser. No. 10/606,910, filed Jun. 26, 2003, now U.S. Pat. No. 7,241,311, issued Jul. 10, 2007, which is a divisional application of U.S. Ser. No. 09/863,546, filed May 23, 2001, now U.S. Pat. No. 6,609,793, issued Aug. 26, 2003.

FIELD OF INVENTION

The present invention relates to methods of designing ophthalmic lenses that provide the eye with reduced aberrations, as well as lenses capable of providing such visual improvements.

BACKGROUND OF THE INVENTION

It is presently discussed that the visual quality of eyes having an implanted intraocular lens (IOL) is comparable with normal eyes in a population of the same age. Consequently, a 70 year old cataract patient can only expect to obtain the visual quality of a non-cataracteous person of the same age after surgical implantation of an intraocular lens, although such lenses objectively have been regarded as optically superior to the natural crystalline lens. This result is likely to be explained by the fact that present IOLs are not adapted to compensate for defects of the optical system of the human eye, namely optical aberrations. Age-related defects of the eye have recently been investigated and it is found that contrast sensitivity significantly declines in subjects older than 50 years. These results seem to comply with the above-mentioned discussion, since the contrast sensitivity measurements indicate that individuals having undergone cataract surgery with lens implantation lens will not obtain a better contrast sensitivity than non-cataracteous persons of an average age of about 60 to 70 years.

Even if intraocular lenses aimed at substituting the defective cataract lens and other ophthalmic lenses, such as conventional contact lenses, have been developed with excellent optical quality as isolated elements, it is obvious that they fail to correct for a number of aberration phenomena of the eye including age-related aberration defects.

U.S. Pat. No. 5,777,719 (Williams et al.) discloses a method and an apparatus for accurately measuring higher order aberrations of the eye as an optical system with wavefront analysis. By using a Hartmann-Shack wavefront sensor, it is possible to measure higher order aberrations of the eye and use such data to find compensation for these aberrations and thereby obtain sufficient information for the design of an optical lens, which can provide a highly improved optical performance. The Hartmann-Shack sensor provides means for analyzing light reflected from a point on the retina of the eye of a subject. The wavefront in the plane of the pupil is recreated in the plane of the lenslet array of the Hartmann-Shack sensor. Each lenslet in the array is used to form an aerial image of the retinal point source on a CCD camera located at the focal plane of the array. The wave aberration of the eye, in the form resulting from a point source produced on the retina by a laser beam, displaces each spot by an amount proportional to the local slope of the wavefront at each of the lenslets. The output from the CCD camera is sent to a computer, which then performs calculations to fit slope data to the first derivatives of 66 Zernike polynomials. From these calculations, coefficients for weighting the Zernike polynomials are obtained. The sum of the weighted Zernike polynomials represents a reconstructed wavefront distorted by the aberrations of the eye as an optical system. The individual Zernike polynomial terms will then represent different modes of aberration.

U.S. Pat. No. 5,050,981 (Roffman) discloses another method for designing a lens by calculating modulation transfer functions from tracing a large number of rays through the lens-eye system and evaluating the distribution density of the rays in the image position. This is repeatedly performed by varying at least one lens surface until a lens is found which results in a sharp focus and a maximum modulation transfer function.

U.S. Pat. No. 6,224,211 (Gordon) describes a method of improving the visual acuity of the human eye by successively fitting aspheric lenses to the cornea and thereby finding a lens that can reduce spherical aberration of the whole individual eye.

The methods referred to above for designing are suitable for the design of contact lenses or other correction lenses for the phakic eye which can be perfected to compensate for the aberration of the whole eye system. However, to provide improved intraocular lenses aimed to replace the natural crystalline lens, it would be necessary to consider the aberrations of the individual parts of the eye.

U.S. Pat. No. 6,050,687 (Bille et al) refers to a method wherein the refractive properties of the eye are measured and wherein consideration is taken to the contribution of the individual surfaces of the eye to the total wavefront aberrations. The method described herein particularly aims at analyzing the topography of the posterior corneal surface in order to improve refractive correction techniques.

There has recently been a focus on studying the aberrations of the eye, including a number of studies of the development of these aberrations as a function of age. In two particular studies, the development of the components of the eye were examined separately, leading to the conclusion that the optical aberrations of the individual components of younger eyes cancel each other out, see Optical Letters, 1998, Vol. 23(21), pp. 1713-1715 and IOVS, 2000, Vol. 41(4), 545. The article of S. Patel et al in Refractive & Corneal Surgery, 1993, Vol. 9, pages 173-181 discloses the asphericity of posterior corneal surfaces. It is suggested that the corneal data can be used together with other ocular parameters to predict the power and the asphericity of an intraocular lens with the purpose of maximizing the optical performances of the future pseudophakic eye. Furthermore, it was also recently observed by Antonio Guirao and Pablo Artal in IOVS, 1999, Vol. 40(4), S535 that the shape of the cornea changes with age and becomes more spherical. These studies indicate that the cornea in the subjects provides a positive spherical aberration, which increases slightly with the age. On the other hand, the rotationally symmetric aberration of the anterior corneal surface does not seem to be different between younger and older eye according to results found by T Oshika et al in Investigative Ophthalmology and Visual Science, 1999, Vol. 40, pp. 1351-1355. In Vision Research, 1998, 38(2), pp. 209-229, A Glasser et al. investigated the spherical aberration of natural crystalline lenses from eyes obtained from an eye bank after the cornea has been removed. According to the laser scanner optical method used herein it was found that the spherical aberration from an older lens (66 years) shows positive spherical aberration, whereas a 10-year-old lens shows negative spherical aberration. In addition, Vision Research, 2001, 41, pp. 235-243 (G Smith et al) discloses that the natural crystalline lens appears to have negative spherical aberration when in the relaxed state. Smith et al suggest that because older eyes have a larger aberration, it is likely that the spherical aberration of the crystalline lens becomes less negative with age.

In Ophthal. Physiol. Opt., 1991, Vol. 11, pp. 137-143 (D A Atchison) it is discussed how to reduce spherical aberrations in intraocular lenses by aspherizing the lens surface. The methods outlined by Atchison are based on geometric transferring calculations, which do not consider diffraction effects and any variations in refractive index along the ray path in inhomogeneous elements. These calculations will lead to errors close to the diffraction limit. Also in WO 98/31299 (Technomed) a ray tracing method is outlined according to which the refraction of the cornea is attempted to be considered for the design of an intraocular lens. In view of the foregoing, it is apparent that there is a need for ophthalmic lenses that are better adapted or compensated to the aberrations of the individual surfaces of the eye and are capable of better correcting aberrations other than defocus and astigmatism, as provided by conventional ophthalmic lenses.

DESCRIPTION OF THE INVENTION

It is an object of the invention to provide for methods that result in obtaining an ophthalmic lens, which provides the eye with reduced aberrations.

It is another object of the invention to provide methods of obtaining an intraocular lens capable of reducing the aberration of the eye after its implantation into the eye.

It is a further object to provide for methods of obtaining an intraocular lens capable of compensating the aberrations resulting from optical irregularities in the corneal surfaces.

It is a still further object of the present invention to provide an intraocular lens which is capable of restoring a wavefront deviating from sphericity into a substantially more spherical wavefront.

It is a also an object of the present invention to provide an intraocular lens which is capable of correcting for mean optical irregularities and imperfections found in a particular group of people and thereby provide a lens with improved optical performance for an individual belonging to the same group.

The present invention generally relates to an ophthalmic lens and to methods of obtaining said ophthalmic lens that is capable of reducing the aberrations of the eye. By aberrations in this context is meant wavefront aberrations. This is based on the understanding that a converging wavefront must be perfectly spherical to form a point image, i.e. if a perfect image shall be formed on the retina of the eye, the wavefront having passed the optical surfaces of the eye, such as the cornea and a natural or artificial lens, must be perfectly spherical. An aberrated image will be formed if the wavefront deviates from being spherical. In this context the term non-spherical surface will refer to rotationally symmetric, asymmetric and/or irregular surfaces, i.e. all surfaces differing from a sphere. The wavefront aberrations can be expressed in mathematical terms in accordance with different approximate models as is explained in textbook references, such as M. R. Freeman, Optics, Tenth Edition, 1990.

In a first embodiment, the present invention is directed to a method of designing an intraocular lens capable of reducing aberrations of the eye after its implantation. The method comprises a first step of characterizing at least one corneal surface as a mathematical model and by employing the mathematical model calculating the resulting aberrations of the corneal surface. An expression of the corneal aberrations is thereby obtained, i.e. the wavefront aberrations of a spherical wavefront having passed such a corneal surface. Dependent on the selected mathematical model different routes to calculate the corneal aberrations can be taken. Preferably, the corneal surface is characterized as a mathematical model in terms of a conoid of rotation or in terms of polynomials or a combination thereof. More preferably, the corneal surface is characterized in terms of a linear combination of polynomials. The second step of the method is to select the power of the intraocular lens, which is done according to conventional methods for the specific need of optical correction of the eye, for example the method described in U.S. Pat. No. 5,968,095 From the information of steps one and two an intraocular lens is modeled, such that a wavefront from an optical system comprising said lens and corneal model obtains reduced aberrations. The optical system considered when modeling the lens typically includes the cornea and said lens, but in the specific case it can also include other optical elements including the lenses of spectacles, or an artificial correction lens, such as a contact lens, a corneal inlay implant or an implantable correction lens depending on the individual situation.

Modeling the lens involves selection of one or several lens parameters in a system which contributes to determine the lens shape of a given, pre-selected refractive power. This typically involves the selection of the anterior radius and surface shape, posterior radius and surface shape, the lens thickness and the refractive index of the lens. In practical terms, the lens modeling can be performed with data based on a conventional spherical lens, such as the CeeOn® lenses from Pharmacia Corp., as exemplified with the CeeOn® Edge (Model 911). In such a case, it is preferred to deviate as little as possible from an already clinically approved model. For this reason, it may be preferred to maintain pre-determined values of the central radii of the lens, its thickness and refractive index, while selecting a different shape of the anterior and/or posterior surface, thus providing one or both of these surfaces to have an nonspherical shape. According to an alternative of the inventive method, the spherical anterior surface of the conventional starting lens is modeled by selecting a suitable aspheric component. Preferably the lens has at least one surface described as a nonsphere or other conoid of rotation. Designing nonspherical surfaces of lenses is a well-known technique and can be performed according to different principles and the description of such surfaces is explained in more detail in our parallel Swedish Patent Application 0000611-4 to which is given reference.

The inventive method can be further developed by comparing wavefront aberrations of an optical system comprising the lens and the model of the average cornea with the wavefront aberrations of the average cornea and evaluating if a sufficient reduction in wavefront aberrations is obtained. Suitable variable parameters are found among the above-mentioned physical parameters of the lens, which can be altered so as to find a lens model, which deviates sufficiently from being a spherical lens to compensate for the corneal aberrations.

The characterization of at least one corneal surface as a mathematical model and thereby establishing a corneal model expressing the corneal wavefront aberrations is preferably performed by direct corneal surface measurements according to well-known topographical measurement methods which serve to express the surface irregularities of the cornea in a quantifiable model that can be used with the inventive method. Corneal measurements for this purpose can be performed by the ORBSCAN® videokeratograph, as available from Orbtech, or by corneal topography methods, such as EyeSys® from Premier Laser Systems. Preferably, at least the front corneal surface is measured and more preferably both front and rear corneal surfaces are measured and characterized and expressed together in resulting wavefront aberration terms, such as a linear combination of polynomials which represent the total corneal wavefront aberrations. According to one important aspect of the present invention, characterization of corneas is conducted on a selected population with the purpose of expressing an average of corneal wavefront aberrations and designing a lens from such averaged aberrations. Average corneal wavefront aberration terms of the population can then be calculated, for example as an average linear combination of polynomials and used in the lens design method. This aspect includes selecting different relevant populations, for example in age groups, to generate suitable average corneal surfaces. Advantageously, lenses can thereby be provided which are adapted to an average cornea of a population relevant for an individual elected to undergo cataract surgery or refractive correction surgery including implantation of an IOL or corneal inlays. The patient will thereby obtain a lens that gives the eye substantially less aberrations when compared to a conventional spherical lens.

Preferably, the mentioned corneal measurements also include the measurement of the corneal refractive power. The power of the cornea and the axial eye length are typically considered for the selection of the lens power in the inventive design method.

Also preferably, the wavefront aberrations herein are expressed as a linear combination of polynomials and the optical system comprising the corneal model and modeled intraocular lens provides for a wavefront having obtained a substantial reduction in aberrations, as expressed by one or more such polynomial terms. In the art of optics, several types of polynomials are available to skilled persons for describing aberrations. Suitably, the polynomials are Seidel or Zernike polynomials. According to the present invention Zernike polynomials preferably are employed.

The technique of employing Zernike terms to describe wavefront aberrations originating from optical surfaces deviating from being perfectly spherical is a state of the art technique and can be employed for example with a Hartmann-Shack sensor as outlined in J. Opt. Soc. Am., 1994, Vol. 11(7), pp. 1949-57. It is also well established among optical practitioners that the different Zernike terms signify different aberration phenomena including defocus, astigmatism, coma and spherical aberration up to higher aberrations. In an embodiment of the present method, the corneal surface measurement results in that a corneal surface is expressed as a linear combination of the first 15 Zernike polynomials. By means of a raytracing method, the Zernike description can be transformed to a resulting wavefront (as described in Equation (1)), wherein $Z_i$ is the i-th Zernike term and $a_i$ is the weighting coefficient for this term. Zernike polynomials are a set of complete orthogonal polynomials defined on a unit circle. Below, Table 1 shows the first 15 Zernike terms and the aberrations each term signifies.

$$z(\rho, \theta) = \sum_{i=1}^{15} a_i Z_i \quad (1)$$

In equation (1), $\rho$ and $\theta$ represent the normalized radius and the azimuth angle, respectively.

TABLE 1

| i | $Z_i(\rho, \theta)$ | |
|---|---|---|
| 1 | 1 | Piston |
| 2 | $2\rho\cos\theta$ | Tilt x |
| 3 | $2\rho\sin\theta$ | Tilt y |
| 4 | $\sqrt{3}(2\rho^2 - 1)$ | Defocus |
| 5 | $\sqrt{6}(\rho^2 \sin 2\theta)$ | Astigmatism $1^{st}$ order (45°) |
| 6 | $\sqrt{6}(\rho^2 \cos 2\theta)$ | Astigmatism $1^{st}$ order (0°) |
| 7 | $\sqrt{8}(3\rho^3 - 2\rho)\sin\theta$ | Coma y |
| 8 | $\sqrt{8}(3\rho^3 - 2\rho)\cos\theta$ | Coma x |
| 9 | $\sqrt{8}(\rho^3 \sin 3\theta)$ | Trifoil 30° |
| 10 | $\sqrt{8}(\rho^3 \cos 3\theta)$ | Trifoil 0° |
| 11 | $\sqrt{5}(6\rho^4 - 6\rho^2 + 1)$ | Spherical aberration |
| 12 | $\sqrt{10}(4\rho^4 - 3\rho^2)\cos 2\theta$ | Astigmatism $2^{nd}$ order (0°) |
| 13 | $\sqrt{10}(4\rho^4 - 3\rho^2)\sin 2\theta$ | Astigmatism $2^{nd}$ order (45°) |
| 14 | $\sqrt{10}(\rho^4 \cos 4\theta)$ | Tetrafoil 0° |
| 15 | $\sqrt{10}(\rho^4 \sin 4\theta)$ | Tetrafoil 22.5° |

Conventional optical correction with intraocular lenses will only comply with the fourth term of an optical system comprising the eye with an implanted lens. Glasses, contact lenses and some special intra ocular lenses provided with correction for astigmatism can further comply with terms five and six and substantially reducing Zernike polynomials referring to astigmatism.

The inventive method further includes to calculate the wavefront aberrations resulting from an optical system comprising said modeled intraocular lens and cornea and expressing it in a linear combination of polynomials and to determine if the intraocular lens has provided sufficient reduction in wavefront aberrations. If the reduction in wavefront aberrations is found to be insufficient, the lens will be re-modeled until one or several of the polynomial terms are sufficiently reduced. Remodeling the lens means that at least one lens design parameter is changed. These include the anterior surface shape and central radius, the posterior surface shape and central radius, the thickness of the lens and its refractive index. Typically, such remodeling includes changing the shape of a lens surface so it deviates from being a spherical. There are several tools available in lens design that are useful to employ with the design method, such as OSLO version 5 see Program Reference, Chapter 4, Sinclair Optics 1996. The format of the Zernike polynomials associated with this application are listed in Table 1.

According to a preferred aspect of the first embodiment, the inventive method comprises expressing at least one corneal surface as a linear combination of Zernike polynomials and thereby determining the resulting corneal wavefront Zernike coefficients, i.e. the coefficient of each of the individual Zernike polynomials that is selected for consideration. The lens is then modeled so that an optical system comprising of said model lens and cornea provides a wavefront having a sufficient reduction of selected Zernike coefficients. The method can optionally be refined with the further steps of calculating the Zernike coefficients of the Zernike polynomials representing a wavefront resulting from an optical system comprising the modeled intraocular lens and cornea and determining if the lens has provided a sufficient reduction of the wavefront Zernike coefficients of the optical system of cornea and lens; and optionally re-modeling said lens until a sufficient reduction in said coefficients is obtained. Preferably, in this aspect the method considers Zernike polynomials up to the 4th order and aims to sufficiently reduce Zernike coefficients referring to spherical aberration and/or astigmatism terms. It is particularly preferable to sufficiently reduce the 11th Zernike coefficient of a wavefront front from an optical system comprising cornea and said modeled intraocular lens, so as to obtain an eye sufficiently free from spherical aberration. Alternatively, the design method can also include reducing higher order aberrations and thereby aiming to reduce Zernike coefficients of higher order aberration terms than the $4^{th}$ order.

When designing lenses based on corneal characteristics from a selected population, preferably the corneal surfaces of each individual are expressed in Zernike polynomials describing the surface topography and therefrom the Zernike coefficients of the wavefront aberration are determined. From these results average Zernike wavefront aberration coefficients are calculated and employed in the design method, aiming at a sufficient reduction of selected such coefficients. In an alternative method according to the invention, average values of the Zernike polynomials describing the surface topography are instead calculated and employed in the design method. It is to be understood that the resulting lenses arriving from a design method based on average values from a large population have the purpose of substantially improving visual quality for all users. A lens having a total elimination of a wavefront aberration term based on an average value may consequently be less desirable and leave certain individuals with an inferior vision than with a conventional lens. For this reason, it can be suitable to reduce the selected Zernike coefficients only to certain degree of the average value.

According to another approach of the inventive design method, corneal characteristics of a selected population and the resulting linear combination of polynomials, e.g. Zernike polynomials, expressing each individual corneal aberration can be compared in terms of coefficient values. From this result, a suitable value of the coefficients is selected and employed in the inventive design method for a suitable lens. In a selected population having aberrations of the same sign such a coefficient value can typically be the lowest value within the selected population and the lens designed from this value would thereby provide improved visual quality for all individuals in the group compared to a conventional lens. One embodiment of the method comprises selecting a representative group of patients and collecting corneal topographic data for each subject in the group. The method comprises further transferring said data to terms representing the corneal surface shape of each subject for a preset aperture size representing the pupil diameter. Thereafter a mean value of at least one corneal surface shape term of said group is calculated, so as to obtain at least one mean corneal surface shape term. Alternatively or complementary a mean value of at least one to the cornea corresponding corneal wavefront aberration term can be calculated. The corneal wavefront aberration terms are obtained by transforming corresponding corneal surface shape terms using a raytrace procedure. From said at least one mean corneal surface shape term or from said at least one mean corneal wavefront aberration term an ophthalmic lens capable of reducing said at least one mean wavefront aberration term of the optical system comprising cornea and lens is designed.

In one preferred embodiment of the invention the method further comprises designing an average corneal model for the group of people from the calculated at least one mean corneal surface shape term or from the at least one mean corneal wavefront aberration term. It also comprises checking that the designed ophthalmic lens compensates correctly for the at least one mean aberration term. This is done by measuring these specific aberration terms of a wavefront having traveled through the model average cornea and the lens. The lens is redesigned if said at least one aberration term has not been sufficiently reduced in the measured wavefront.

Preferably one or more surface descriptive (asphericity describing) constants are calculated for the lens to be designed from the mean corneal surface shape term or from the mean corneal wavefront aberration terms for a predetermined radius. The spherical radius is determined by the refractive power of the lens.

The corneal surfaces are preferably characterized as mathematical models and the resulting aberrations of the corneal surfaces are calculated by employing the mathematical models and raytracing techniques. An expression of the corneal wavefront aberrations is thereby obtained, i.e. the wavefront aberrations of a wavefront having passed such a corneal surface. Dependent on the selected mathematical model different routes to calculate the corneal wavefront aberrations can be taken. Preferably, the corneal surfaces are characterized as mathematical models in terms of a conoid of rotation or in terms of polynomials or a combination thereof. More preferably, the corneal surfaces are characterized in terms of linear combinations of polynomials.

In one embodiment of the invention, the at least one non-spheric surface of the lens is designed such that the lens, in the context of the eye, provides to a passing wavefront at least one wavefront aberration term having substantially the same value but with opposite sign to a mean value of the same aberration term obtained from corneal measurements of a selected group of people, to which said patient is categorized. Hereby a wavefront arriving from the cornea of the patient's eye obtains a reduction in said at least one aberration term provided by the cornea after passing said lens. The used expression 'in the context of the eye' can mean both in the real eye and in a model of an eye. In a specific embodiment of the invention, the wavefront obtains reduced aberration terms expressed in rotationally symmetric Zernike terms up to the fourth order. For this purpose, the surface of the ophthalmic lens is designed to reduce a positive spherical aberration term of a passing wavefront. The consequence of this is that if the cornea is a perfect lens and thus not will give rise to any wavefront aberration terms the ophthalmic lens will provide the optical system comprising the cornea and the ophthalmic lens with a negative wavefront spherical aberration term. In this text positive spherical aberration is defined such that a spherical surface with positive power produces positive spherical aberration. Preferably the lens is adapted to compensate for spherical aberration and more preferably it is adapted to compensate for at least one term of a Zernike polynomial representing the aberration of a wavefront, preferably at least the $11^{th}$ Zernike term, see Table 1.

The selected groups of people could for example be a group of people belonging to a specific age interval, a group of people who will undergo a cataract surgical operation or a group of people who have undergone corneal surgery including but not limited to LASIK (laser in situ keratomileusis), RK (radial keratotomy) or PRK (photorefractive keratotomy). The group could also be a group of people who have a specific ocular disease or people who have a specific ocular optical defect.

The lens is also suitably provided with an optical power. This is done according to conventional methods for the specific need of optical correction of the eye. Preferably the refractive power of the lens is less than or equal to 30 diopters. An optical system considered when modeling the lens to compensate for aberrations typically includes the average cornea and said lens, but in the specific case it can also include other optical elements including the lenses of spectacles, or an artificial correction lens, such as a contact lens, a corneal inlay or an implantable correction lens depending on the individual situation.

In an especially preferred embodiment the ophthalmic lens is designed for people who will undergo a cataract surgery. In this case it is has been shown that the average cornea from such a population is represented by a prolate surface following the formula:

$$z = \frac{(1/R)r^2}{1+\sqrt{1-\left(\frac{1}{R}\right)^2(cc+1)r^2}} + adr^4 + aer^6$$

wherein, (i) the conical constant cc has a value ranging between −1 and 0

(ii) R is the central lens radius and (iii) ad and ae are aspheric polynomial coefficients additional to the conical constant.

In these studies the conic constant of the prolate surface ranges between about −0.05 for an aperture size (pupillary diameter) of 4 mm to about −0.18 for an aperture size of 7 mm. Accordingly an ophthalmic lens suitable to improve visual quality by reducing at least spherical aberration for a cataract patient based on an average corneal value will have a prolate surface following the formula above. Since cornea generally produces a positive spherical aberration to a wavefront in the eye, an ophthalmic lens for implantation into the eye will have negative spherical aberration terms while following the mentioned prolate curve. As will discussed in more detail in the exemplifying part of the specification, it has been found that an intraocular lens that can correct for 100% of a mean spherical aberration has a conical constant (cc) with a value of less than 0 (representing a modified conoid surface), with an exact value dependent on the design pupillary diameter and the selected refractive power. For example, a 6 mm diameter aperture will provide a 22 diopter lens with conical constant value of about −1.03. In this embodiment, the ophthalmic lens is designed to balance the spherical aberration of a cornea that has a Zernike polynomial coefficient representing spherical aberration of the wavefront aberration with a value in the interval from 0.000156 mm to 0.001948 mm for a 3 mm aperture radius, 0.000036 mm to 0.000448 mm for a 2 mm aperture radius, 0.0001039 mm to 0.0009359 mm for a 2.5 mm aperture radius and 0.000194 mm to 0.00365 mm for a 3.5 mm aperture radius using polynomials expressed in OSLO format. These values were calculated for a model cornea having a single surface with a refractive index of the cornea of 1.3375. It is possible to use optically equivalent model formats of the cornea without departing from the scope of the invention. For example multiple surface corneas or corneas with different refractive indices could be used. The lower values in the intervals are here equal to the measured average value for that specific aperture radius minus one standard deviation. The higher values are equal to the measured average value for each specific aperture radius plus three standard deviations. The used average values and standard deviations are shown in tables 8, 9, 10 and 11. The reason for selecting only minus one SD (=Standard Deviation) while selecting plus three SD is that in this embodiment it is convenient to only compensate for positive corneal spherical aberration and more than minus one SD added to the average value would give a negative corneal spherical aberration.

According to one embodiment of the invention the method further comprises the steps of measuring the at least one wavefront aberration term of one specific patient's cornea and determining if the selected group corresponding to this patient is representative for this specific patient. If this is the case the selected lens is implanted and if this is not the case a lens from another group is implanted or an individual lens for this patient is designed using this patients corneal description as a design cornea. These method steps are preferred since then patients with extreme aberration values of their cornea can be given special treatments.

According to another embodiment, the present invention is directed to the selection of an intraocular lens of refractive power, suitable for the desired optical correction that the patient needs, from a plurality of lenses having the same power but different aberrations. The selection method is similarly conducted to what has been described with the design method and involves the characterizing of at least one corneal surface with a mathematical model by means of which the aberrations of the corneal surface is calculated. The optical system of the selected lens and the corneal model is then evaluated so as to consider if sufficient reduction in aberrations is accomplished by calculating the aberrations of a wavefront arriving from such a system. If an insufficient correction is found a new lens is selected, having the same power, but different aberrations. The mathematical models employed herein are similar to those described above and the same characterization methods of the corneal surfaces can be employed.

Preferably, the aberrations determined in the selection are expressed as linear combinations of Zernike polynomials and the Zernike coefficients of the resulting optical system comprising the model cornea and the selected lens are calculated. From the coefficient values of the system, it can be determined if the intraocular lens has sufficiently balanced the corneal aberration terms, as described by the Zernike coefficients of the optical system. If no sufficient reduction of the desired individual coefficients are found these steps can be iteratively repeated by selecting a new lens of the same power but with different aberrations, until a lens capable of sufficiently reducing the aberrations of the optical system is found. Preferably at least 15 Zernike polynomials up to the $4^{th}$ order are determined. If it is regarded as sufficient to correct for spherical aberration, only the spherical aberration terms of the Zernike polynomials for the optical system of cornea and intraocular lens are corrected. It is to be understood that the intraocular lens shall be selected so a selection of these terms become sufficiently small for the optical system comprising lens and cornea. In accordance with the present invention, the $11^{th}$ Zernike coefficient, $a_{11}$, can be substantially eliminated or brought sufficiently close to zero. This is a prerequisite to obtain an intraocular lens that sufficiently reduces the spherical aberration of the eye. The inventive method can be employed to correct for other types of aberrations than spherical aberration by considering other Zernike coefficients in an identical manner, for example those signifying astigmatism, coma and higher order aberrations. Also higher order aberrations can be corrected dependent on the number of Zernike polynomials elected to be a part of the modeling, in which case a lens can be selected capable of correcting for higher order aberrations than the $4^{th}$ order.

According to one important aspect, the selection method involves selecting lenses from a kit of lenses having lenses with a range of power and a plurality of lenses within each power having different aberrations. In one example the lenses within each power have anterior surfaces with different aspherical components. If a first lens does not exhibit sufficient reduction in aberration, as expressed in suitable Zernike coefficients, then a new lens of the same power, but with a different surface (aspheric component) is selected. The selection method can if necessary be iteratively repeated until the best lens is found or the studied aberration terms are reduced below a significant borderline value. In practice, the Zernike terms obtained from the corneal examination will be directly obtained by the ophthalmic surgeon and by means of an algorithm they will be compared to known Zernike terms of the lenses in the kit. From this comparison the most suitable lens in the kit can be found and implanted. Alternatively, the method can be conducted before cataract surgery and data from the corneal estimation is sent to a lens manufacturer for production of an individually tailored lens.

The present invention further pertains to an intraocular lens having at least one nonspherical surface capable of transferring a wavefront having passed through the cornea of the eye into a substantially spherical wavefront with its center at the retina of the eye. Preferably, the wavefront is substantially spherical with respect to aberration terms expressed in rotationally symmetric Zernike terms up to the fourth order.

In accordance with an especially preferred embodiment, the invention relates to an intraocular lens, which has at least one surface, when expressed as a linear combination of Zernike polynomial terms using the normalized format, that has a negative $11^{th}$ term of the fourth order with a Zernike coefficient $a_{11}$ that that can balance a positive such term of the cornea, to obtain sufficient reduction of the spherical aberration of the eye after implantation. In one aspect of this embodiment, the Zernike coefficient $a_{11}$ of the lens is determined so as to compensate for an average value resulting from a sufficient number of estimations of the Zernike coefficient $a_{11}$ in several corneas. In another aspect, the Zernike coefficient $a_{11}$ is determined to compensate for the individual corneal coefficient of one patient. The lens can accordingly be tailored for an individual with high precision.

The invention further relates to another method of providing a patient with an intraocular lens, which at least partly compensates for the aberrations of the eye. This method comprises removing the natural lens from the eye. Surgically removing the impaired lens can be performed by using a conventional phacoemulsification method. The method further comprises measuring the aberrations of the aphakic eye, not comprising a lens, by using a wavefront sensor. Suitable methods for wavefront measurements are found in J. Opt. Soc. Am., 1994, Vol. 11(7), pp. 1949-57 by Liang et. al. Furthermore, the method comprises selecting from a kit of lenses a lens that at least partly compensates for the measured aberrations and implanting said lens into the eye. The kit of lenses comprises lenses of different power and different aberrations and finding the most suitable lens can be performed in a manner as earlier discussed. Alternatively, an individually designed lens for the patient can be designed based on the wavefront analysis of the aphakic eye for subsequent implantation. This method is advantageous, since no topographical measurements of the cornea are and the whole cornea, including the front and back surfaces, is automatically considered.

The lenses according to the present invention can be manufactured with conventional methods. In one embodiment they are made from soft, resilient material, such as silicones or hydrogels. Examples of such materials suitable for foldable intraocular lenses are found in U.S. Pat. No. 5,444,106 or in U.S. Pat. No. 5,236,970. Manufacturing of nonspherical silicone lenses or other foldable lenses can be performed according to U.S. Pat. No. 6,007,747. Alternatively, the lenses according to the present invention can be made of a more rigid material, such as poly(methyl)methacrylate. The skilled person can readily identify alternative materials and manufacturing methods, which will be suitable to employ to produce the inventive aberration reducing lenses.

DETAILED DESCRIPTION OF THE INVENTION

EXAMPLE 1

Figure 1:
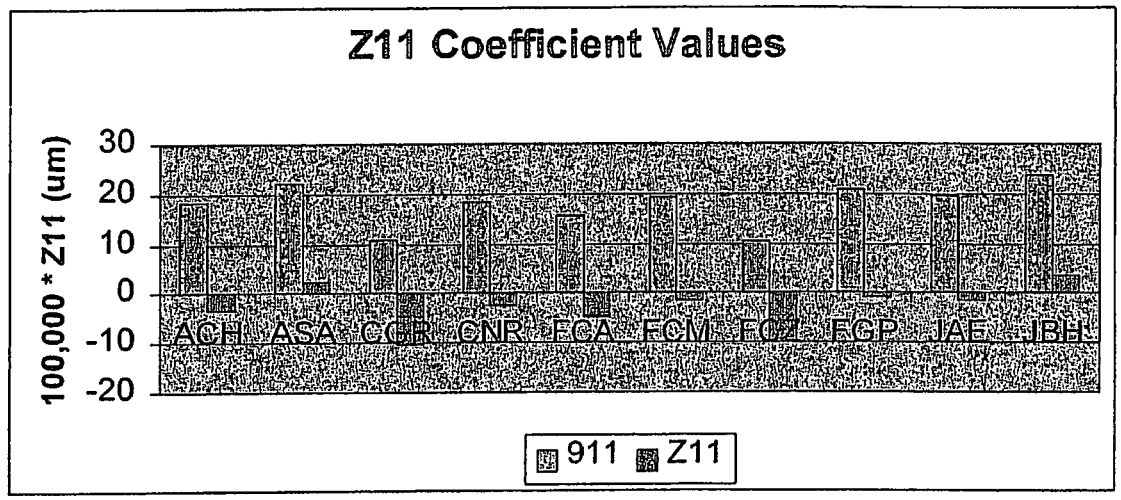
FIG. 1 shows a comparison of the $a_{11}$ ("Z11") Zernike coefficient values for 10 subjects if implanted with CeeOn® 911 lenses and the inventive averaged ("Z11") lens.

A sample set of 10 corneal surfaces from individuals were described using Zernike polynomials. The sag data of the corneas was determined using the real height data measured with a Humphrey Atlas corneal topographer. The corneal topographer measures the height ($z_i$) at a discrete number of points. The corneal surface can then be expressed as a linear combination of the first 15 Zernike polynomials (as described in Equation 1, above), where $Z_i$ is the ith Zernike polynomial and $a_i$ is the weighting coefficient for this polynomial. The Zernike polynomials are a set of complete orthogonal polynomials defined on a unit circle. These polynomials as listed in Table 1 above and the weighting coefficients ($a_i$) are calculated from the height data using a Grahm-Schmidt orthogonalization procedure. The Zernike coefficients ($a_i$) for the 10 sample corneas are listed in Table 2 in mm.

TABLE 2

The Zernike coefficients for the 10 individual corneal surfaces in mm.

|  | ACH | ASA | CGR | CNR | FCA | FCM | FCZ | FGP | JAE | JBH |
|---|---|---|---|---|---|---|---|---|---|---|
| a1 | −7.713337 | −6.698643 | −7.222353 | −7.169027 | −7.001356 | −7.322624 | −7.03713 | −7.84427 | −7.582005 | −6.890056 |
| a2 | 0.000271 | −0.000985 | 0.000386 | −0.000519 | 0.000426 | −0.000094 | −0.000236 | −0.00056 | −0.000344 | −0.000155 |
| a3 | 0.000478 | −0.000002 | −0.000847 | 0.000996 | −0.000393 | 0.000045 | 0.000454 | 0.000347 | 0.000246 | −0.000558 |
| a4 | 0.073309 | 0.083878 | 0.077961 | 0.078146 | 0.080111 | 0.077789 | 0.079987 | 0.072595 | 0.075803 | 0.081415 |
| a5 | −0.000316 | −0.000753 | 0.000119 | 0.000347 | −0.001197 | 0.00022 | −0.000071 | 0.000686 | −0.000388 | −0.000269 |

TABLE 2-continued

The Zernike coefficients for the 10 individual corneal surfaces in mm.

|     | ACH       | ASA       | CGR       | CNR       | FCA       | FCM       | FCZ       | FGP       | JAE       | JBH       |
|-----|-----------|-----------|-----------|-----------|-----------|-----------|-----------|-----------|-----------|-----------|
| a6  | 0.001661  | 0.000411  | −0.000148 | −0.000386 | 0.000314  | 0.000669  | 0.00079   | −0.00048  | 0.001688  | 0.001492  |
| a7  | 0.000193  | 0.00006   | −0.000295 | 0.000324  | −0.000161 | −0.000058 | 0.000148  | 0.00014   | 0.000104  | −0.000227 |
| a8  | 0.000098  | −0.000437 | 0.000146  | −0.00018  | 0.000147  | 0.000039  | −0.000076 | −0.00025  | −0.000173 | −0.000116 |
| a9  | −0.000091 | −0.000168 | −0.000107 | 0.000047  | −0.000181 | −0.000154 | −0.000043 | 0.000092  | −0.000023 | −0.000109 |
| a10 | −0.000055 | 0.000139  | −0.000132 | −0.000149 | 0.000234  | −0.000228 | 0.000244  | −8.2E−05  | −0.000004 | 0.000065  |
| a11 | 0.000277  | 0.000394  | 0.000203  | 0.000305  | 0.000285  | 0.000315  | 0.000213  | 0.000308  | 0.000309  | 0.0004    |
| a12 | −0.000019 | −0.000105 | 0.000025  | 0.00007   | −0.000058 | −0.000033 | 0.00009   | −2E−06    | −0.000115 | −0.00011  |
| a13 | 0.000048  | 0.000032  | 0.000085  | 0.000017  | 0.000039  | 0.000059  | 0.000022  | 0.000101  | −0.000042 | −0.000052 |
| a14 | −0.000067 | 0.000041  | −0.000081 | −0.000049 | 0.000118  | −0.000108 | 0.000127  | −1.9E−05  | −0.000068 | 0.00001   |
| a15 | −0.000048 | −0.000075 | −0.000073 | −0.000019 | −0.000036 | −0.000119 | −0.000021 | 0.000022  | −0.000013 | −0.000048 |

These wavefront aberration coefficients can be calculated using optical design software such as OSLO (Sinclair Optics). Table 3 shows the results of calculating the wavefront aberration for subject FCM. (N.B. The normalization factor for the polynomials used in OSLO is different from those shown in Table 3. This difference has been incorporated into the coefficient values.)

TABLE 3

The corneal aberration coefficients in mm calculated for subject FCM using OSLO (N.B. OSLO numbering order)

| Aberration Coefficients for FCM (OSLO) | |
|---|---|
| A0  | −0.000123 |
| A1  | 4.5960e−07 |
| A2  | 2.0869e−07 |
| A3  | −5.355e−06 |
| A4  | 0.000551 |
| A5  | 0.000182 |
| A6  | 3.7296e−05 |
| A7  | −5.5286e−05 |
| A8  | 0.000116 |
| A9  | −0.000217 |
| A10 | −0.000147 |
| A11 | −3.8151e−05 |
| A12 | 6.1808e−05 |
| A13 | −3.3056e−07 |
| A14 | 4.888e−07 |
| A15 | −1.8642e−06 |
| A16 | −0.000115 |
| A17 | −0.000127 |

EXAMPLE 2

An averaged design embodiment of the inventive lenses has been calculated using the average "old" cornea information provided by Pablo Artal, Murcia, Spain. This data was taken from a population sample of 16 old corneas in which all of the subjects had a visual acuity of 20/30 or better. The corneal surfaces were described using Zernike polynomials for an aperture of 2.0 mm radius ($r_o$). The polynomial coefficients were then used to determine the radius and asphericity values using Equations 2 and 3.

$$R = \frac{r_o^2}{2(2\sqrt{3}\,a_4 - 6\sqrt{5}\,a_{11})} \quad (2)$$

$$K^2 = \frac{8R^3}{r_o^4} 6\sqrt{5}\,a_{11} \quad (3)$$

Note that the asphericity constant, K, describes the surface's variation from a sphere ($K^2 = 1 - e^2$). (i.e. For a sphere K=1 and for a parabola K=0). (cc=$K^2$−1, wherein cc is the conical constant)

Because the cornea surface has only been described for a central diameter of 4 mm, the calculated R and K are also only accurate over the central 4 mm. A pupil size of 4.0 mm is therefore selected for design purposes. This pupil size is reasonable for intraocular lens design purposes.

A 22D CeeOn® 911 lens from Pharmacia Corp was chosen as a starting point for the averaged lens design. For the purpose of comparison, the averaged lenses were also designed to be 22D. (Note that other dioptres would give similar simulation results, provided that the spherical surfaces of the lenses is the same.) The surface information for the starting point eye model is summarized in Table 4. In the conical and aspherical data demonstrated in Table 4, the average conic constant CC is determined for the 10 individual corneas of Example 1.

TABLE 4

Surface data for the starting point of the averaged ("Z11") design

| Surface # | Radius (mm) | Thickness (mm) | Aperture Radius (mm) | Conic Constant | Refractive Index |
|---|---|---|---|---|---|
| Object | — | ∞ | 2.272611 | — | 1.0 |
| 1 (cornea) | 7.573 | 3.6 | 2.272611 | −0.0784* | 1.3375 |
| 2 (pupil) | — | — | 2.0 | — | 1.3375 |
| 3 | — | 0.9 | 2.0 | — | 1.3375 |
| 4 (lens 1) | 11.043 | 1.14 | 3.0 | — | 1.4577 |
| 5 (lens 2) | −11.043 | 17.2097 | 3.0 | — | 1.336 |

*This conic constant for the "average" cornea is taken from the published works of Guirao and Artal The wavefront aberration coefficients in mm for the average cornea are shown in column 1 of Table 5, while the coefficients in mm of the combination of the average cornea and the 911 lens are shown in column 2 of Table 5. Note that the Z11 coefficient (a11) of the average old cornea alone is 0.000220 mm, while the Z11 of this eye implanted with a 911 would be 0.000345 mm.

TABLE 5

Zernike coefficients in mm of the average cornea and the starting point for design (Average cornea + 911)

|    | Average Cornea | Average Cornea + 911 |
|----|----------------|----------------------|
| a1 | 0.000432       | 0.000670             |
| a2 | 0.0            | 0.0                  |
| a3 | 0.0            | 0.0                  |

TABLE 5-continued

Zernike coefficients in mm of the average cornea and
the starting point for design (Average cornea + 911)

|     | Average Cornea | Average Cornea + 911 |
|-----|----------------|----------------------|
| a4  | 0.000650       | 0.00101              |
| a5  | 0.0            | 0.0                  |
| a6  | 0.0            | 0.0                  |
| a7  | 0.0            | 0.0                  |
| a8  | 0.0            | 0.0                  |
| a9  | 0.0            | 0.0                  |
| a10 | 0.0            | 0.0                  |
| a11 | 0.000220       | 0.000345             |
| a12 | 0.0            | 0.0                  |
| a13 | 0.0            | 0.0                  |
| a14 | 0.0            | 0.0                  |
| a15 | 0.0            | 0.0                  |

The averaged lens was optimized to minimize spherical aberration, while maintaining a 22D focal power. The lens material remained the same as in the 22D 911 lens (HRI silicone, the refractive index of which is 1.45 in 77 at 37° C. The resulting design for an equiconvex lens is The averaged lens was optimized to minimize spherical aberration, while maintaining a 22D focal power. The lens material remained the same as in the 22D 911 lens (HRI silicone, the refractive The resulting design for an equiconvex lens is provided in Table 6. The total-eye Z11 coefficient of the average cornea combined with this lens is $-2.42\times10^{-7}$ mm (versus 0.000345 mm for the cornea plus 911 lens).

TABLE 6

Surface data for the starting point of the averaged lens design

| Surface # | Radius (mm) | Thickness (mm) | Aperture Radius (mm) | Conic Constant | $4^{th}$ Order Aspheric Constant | $6^{th}$ Order Aspheric Constant | Refractive Index |
|-----------|-------------|----------------|----------------------|----------------|------------------------------|------------------------------|------------------|
| Object    | —           | ∞              | 2.272611             |                |                              |                              | 1.0              |
| 1 (cornea)| 7.573       | 3.6            | 2.272611             | −0.0784        |                              |                              | 1.3375           |
| 2 (pupil) | —           | —              | 2.0                  | —              |                              |                              | 1.3375           |
| 3         | —           | 0.9            | 2.0                  | —              |                              |                              | 1.3375           |
| 4 (lens 1)| 10.0        | 1.02           | 3.0                  | −2.809         | −0.000762                    | −1.805e−05                   | 1.4577           |
| 5 (lens 2)| −12.0       | 17.2097        | 3.0                  | —              |                              |                              | 1.336            |

Figure 2:
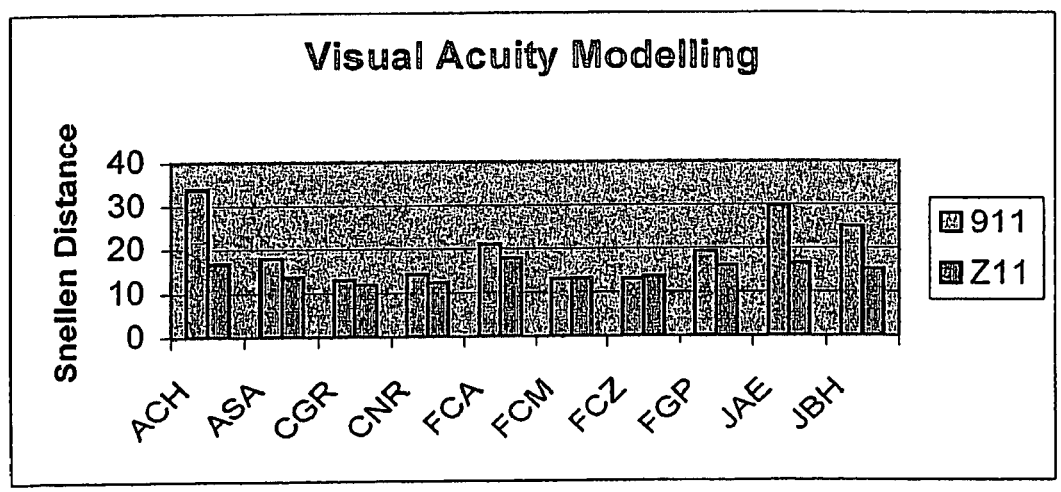
FIG. 2 shows modeled visual acuities of the test subjects with CeeOn® 911 lenses and the inventive averaged ("Z11") lenses.

The corneas of the 10 test subjects were combined in an optical system with both the 911 and the averaged lenses. The resulting total-eye Z11 coefficients are shown in FIG. 1. As demonstrated, in FIG. 1, in each case, the absolute value of the Z11 coefficient was less when the Z11 lens was implanted. Because subjects CGR and FCZ have relatively low levels of corneal spherical aberration to begin with, the total-eye spherical aberration is overcorrected in these two cases. As a result, the sign of the total spherical aberration is noticeably reversed in these two cases, and the amount of spherical aberration is still significant. In every other case, the spherical aberration of the total eye would be essentially 0 after the implantation of a Z11 lens. The visual acuity of each of the 10 test subjects were calculated according to standard methods described in "Visual acuity modeling using optical raytracing of schematic eyes", Greivenkamp et al., American journal of ophthalmology, 120(2), 227-240, (1995), for the implantation of both a 22D 911 lens and a 22D averaged "Z11" lens. The square wave responses were calculated using OSLO™ and a software module was written in Matlab™ to calculate the visual acuity following the above method. The resulting visual acuities are shown in FIG. 2. Out of the 10 cases investigated and shown in FIG. 2, eight subjects had better vision when implanted with the averaged lens according to the present invention. In the cases where the visual acuity decreased their Snellen distance increased by less than 1 ft which would not show up in visual acuity testing.

Figure 3:
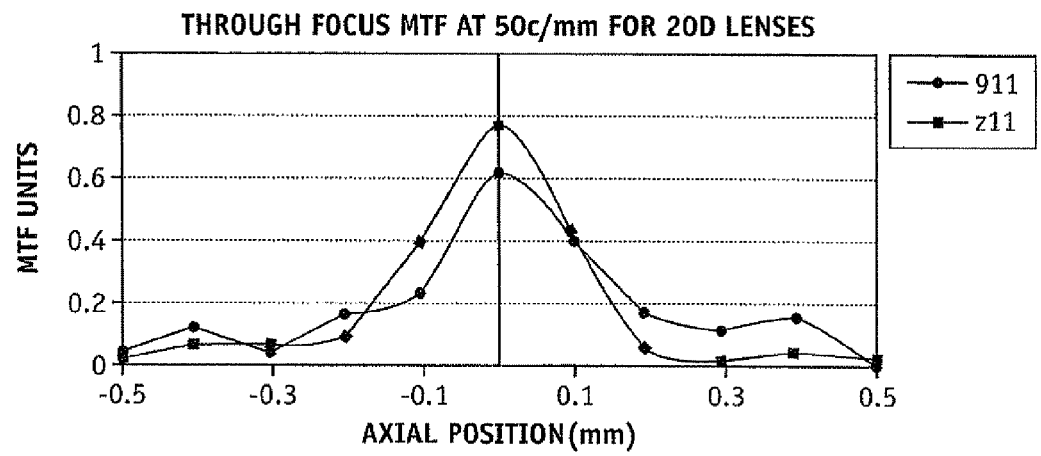
FIG. 3 and FIG. 4 show modulation transfer function comparisons between CeeOn® 911 lenses and the inventive averaged ("Z11") lenses
Figure 4:
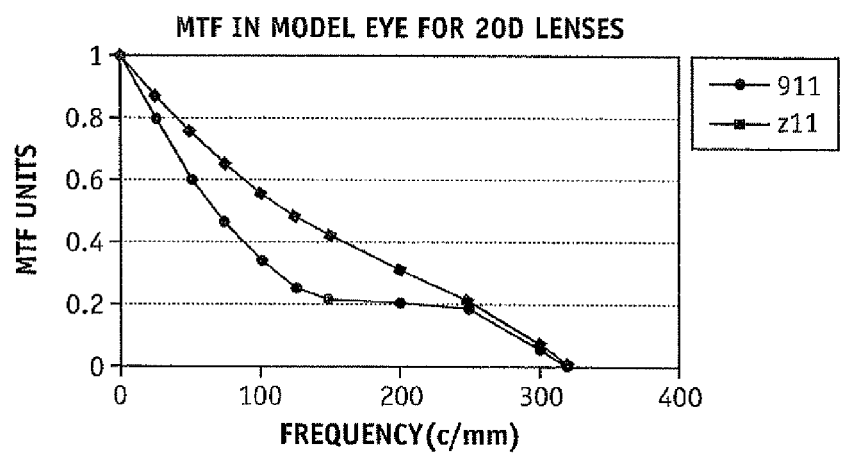
Figure 5:
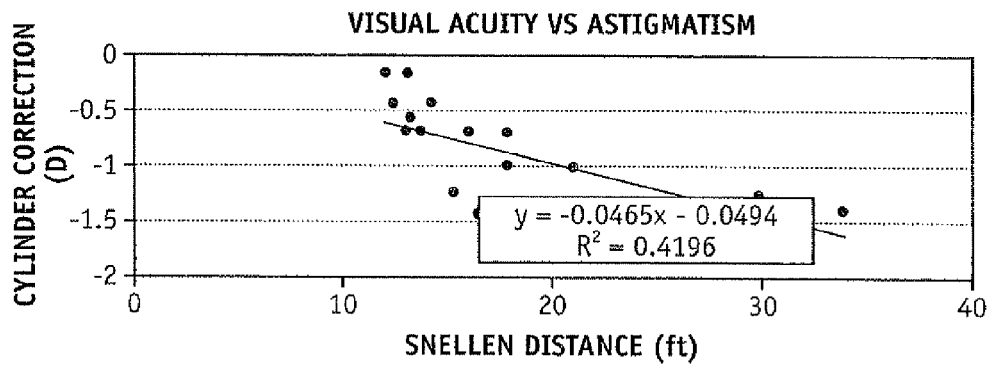
FIG. 5 shows visual acuity plotted as a function of the astigmatism of the lenses according to the model lenses according to the invention.

To be able to assess the optical quality difference between a CeeOn® 911A and averaged lenses according to the present invention, a physical model of the average cornea was designed and manufactured. It is a convex-plano lens of PMMA with an aspheric front surface having a value of 0.000218 for Zernike coefficient a11. This value is almost equal to the value of the calculated average cornea: 0.000220. With the PMMA model cornea MTF measurements were performed on an optical bench in a model eye with the "averaged" Z11 lenses and CeeOn® 911A lenses. Modulation Transfer Function (MTF) measurements are a widely accepted method of quantifying image quality. Through focus MTF measurements at 50 c/mm and a frequency MTF curves focussed at 50 c/mm, in both cases with a 3 mm pupil are shown in the FIG. 3 and FIG. 4, respectively for lenses with an optical power of 20 D. The width of the through focus MTF at 0.2 MTF units is a measure for the depth of focus and is equal for both lenses. The MTF curve focussed at 50 c/mm for "averaged" Z11 lenses is almost diffraction limited and is better than that for CeeOn 911A lenses.

Figure 6:
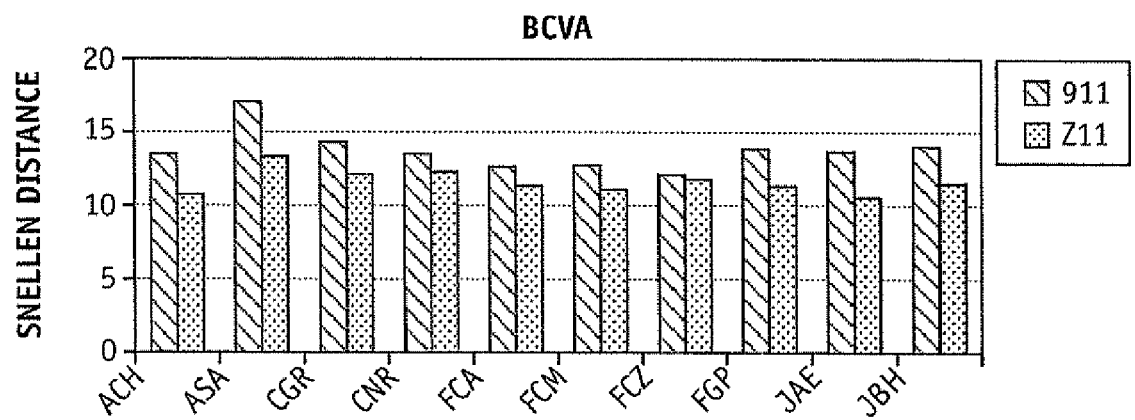
FIG. 6 shows the best corrected visual acuity with the inventive lenses.

The astigmatism of the cornea and the defocus of the system can be corrected by adjusting the Zernike coefficients of the cornea model and the focal position of the system. When this is done and the procedure for calculating visual acuity is repeated the results in FIG. 6 are obtained. They represent a modeled best corrected visual acuity. We now see that, in all cases, after correction for astigmatism and defocus (as in reality would be done with spectacles) the inventive averaged lens produces a higher best corrected visual acuity than the 911 lens of the same dioptre.

EXAMPLE 3

Individually Designed Lenses

As a potential further improvement upon the averaged lens ("Z11 lenses"), an individualized lens ("I11 lenses") was designed for each of four subject corneas employing the same design principles as demonstrated in Example 2. The individual lenses were designed such that the Z11 of the lens balances the Z11 of the individual cornea. The total-eye Z11 coefficients for the I11 lenses are shown in Table 7, together

TABLE 7

The Z11 coefficients in mm of the model eyes
with the 911, Z11 and I11 lenses

Figure 7:
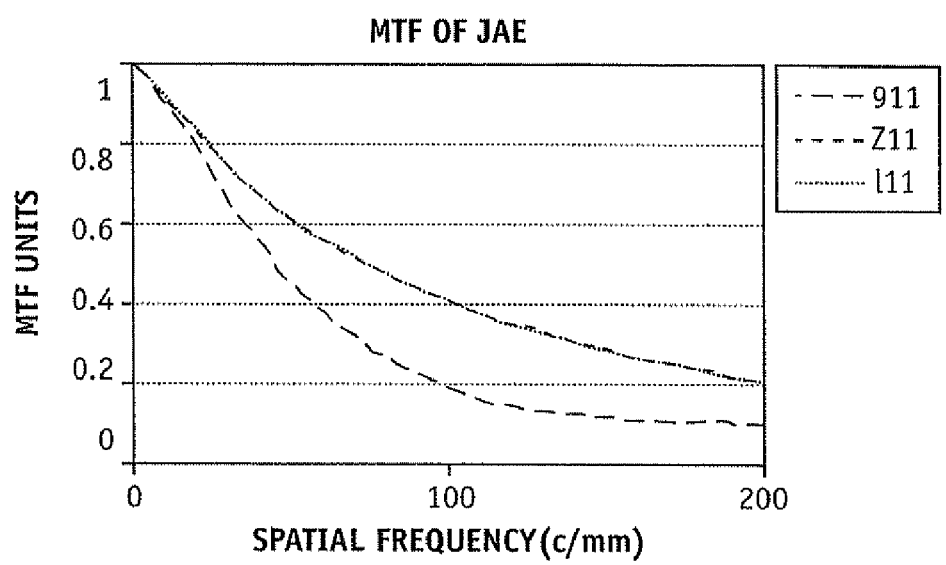
FIGS. 7 and 8 show modulation transfer functions of an individual with an individually designed lens.
Figure 8:
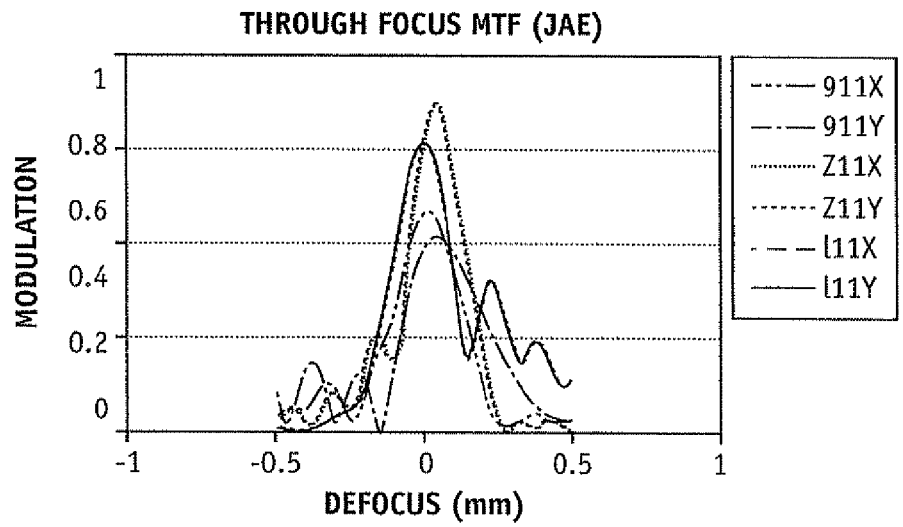

| Subject | 911 | averaged | individual |
|---------|-----|----------|------------|
| CGR | 0.000107 | −0.000101 | −0.000004 |
| FCZ | 0.000105 | −0.000100 | −0.000005 |
| JAE | 0.000195 | −0.000016 | −0.000012 |
| JBH | 0.000238 | 0.000037 | −0.000019 | with the corresponding coefficients for the 911 and the averaged lenses. Furthermore, for each of the 911, Z11 (averaged), and I11 (individual) lenses, the MTF curve at best focussed at 50 c/mm and the through focus MTF at 50 c/mm for subject JAE are plotted below in FIGS. 7 and 8. From FIGS. 7 and 8, it is seen that the MTF at 50 c/mm of eyes implanted with the Z11 and I11 lenses is higher than the MTF of the same eyes implanted with 911 lenses. It can also be seen that the through focus MTF of all of the lenses is satisfactory. The Z11 has as much depth of focus as the 911. However, it is also interesting to note that the I11 does not provide a significant improvement in either MTF or through focus MTF, relative to the Z11 lens.

Figure 9:
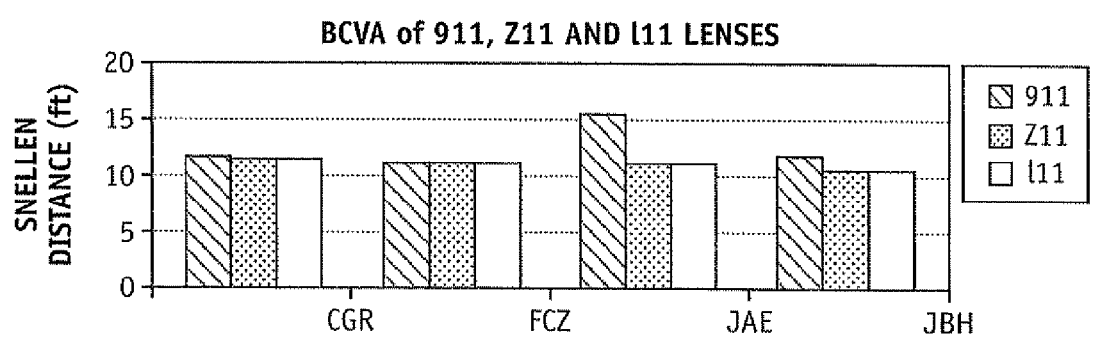
FIG. 9 shows the best corrected visual acuity with individually designed lenses according to the invention.

The visual acuities of the subjects with individualized lenses have also been calculated. FIG. 9 compares these acuities with the visual acuity calculated for the 911 and Z11 lenses.

From FIG. 9, we see that for all 4 subjects, visual acuity is better for both the Z11 and I11 lenses than it is for the 911 lens. We also see that the results with the Z11 and I11 lenses do not differ significantly—the average cornea is relatively accurate for each of the 4 test subjects.

EXAMPLE 4

The design of an ophthalmic lens, which is adapted to reduce the spherical aberration of an average cornea obtained from a group of people will be described in detail here below. The lens will be called the Z11 lens because it compensates for the normalized 11$^{th}$ Zernike term describing spherical aberration of the corneas. It was decided to use a population of potential recipients of the Z11 lens, namely cataract patients.

Figure 10:
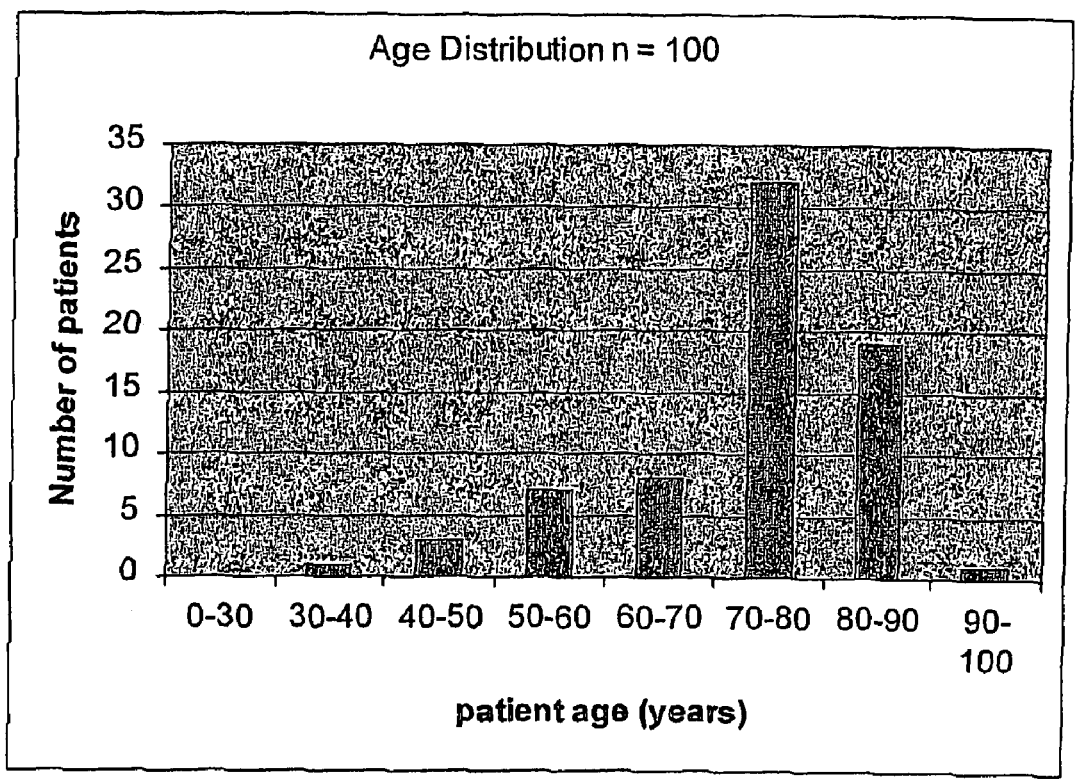
FIG. 10 shows the age distribution of 71 patients used in a study described below in the example part.

Description of the Population:

The population included 71 cataract patients from St. Erik's eye hospital in Stockholm, Sweden. These patients were of ages ranging from 35 to 94 years (as of Apr. 12, 2000). The average age of our population was 73.67 years. A histogram of the age of the population is shown in FIG. 10.

The corneas of the 71 subjects were measured using an Orbscan® (Orbtek, Salt Lake City) device. Orbscan® is a scanning slit-based, corneal and anterior segment topographer that measures both surfaces of the cornea, as well as the anterior lens surface and the iris. Each surface can be displayed as maps of elevation, inclination, curvature, and power.

Figure 11:
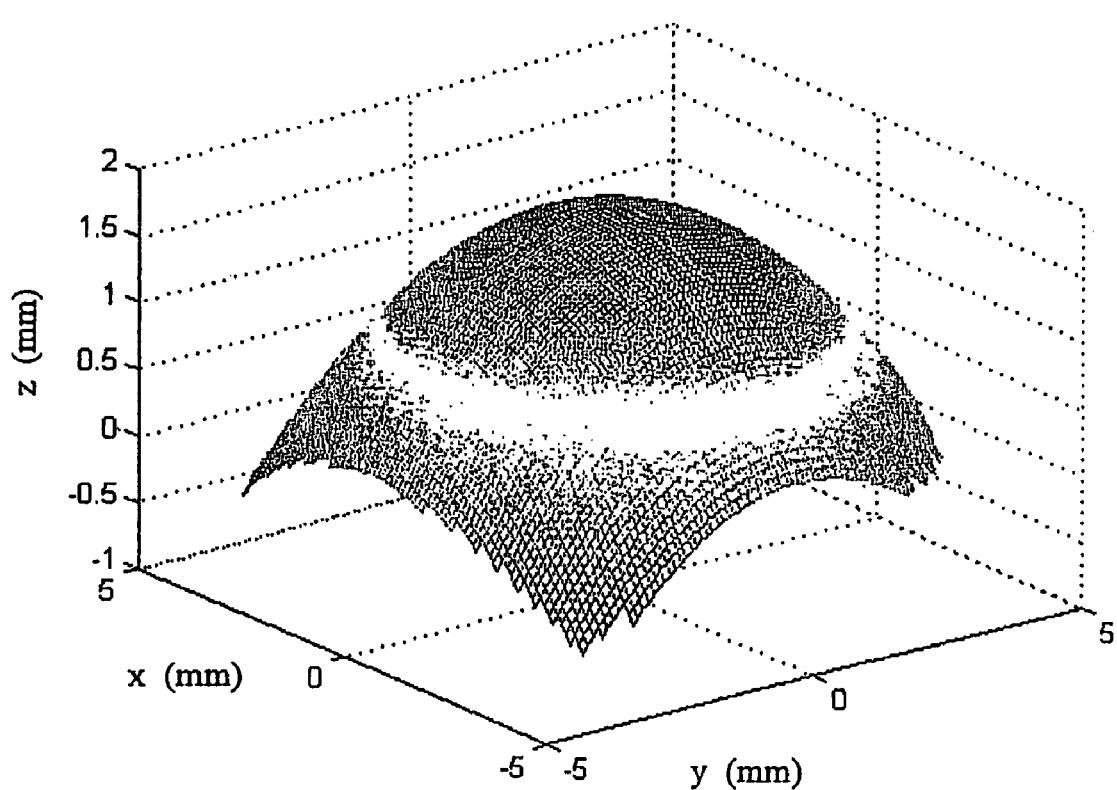
FIG. 11 shows a height map given by an Orbscan® true height data file.

Fitting Algorithm:

The corneal elevation height data (the Cartesian locations of points on the surface of the cornea) for the anterior surface was obtained using the Orbscan®, and used as raw data for the determination of the optical properties of the cornea. The height data from an example Orbscan® file is represented in FIG. 11.

The Cartesian co-ordinates representing the elevation height data are transformed to polar co-ordinates (x,y,z→r,θ,z). In order to describe the surface, this data is then fit to a series of polynomials as described in Equation 1b. The coefficients (a's), or weighting factors, for each polynomial are determined by the fitting procedure resulting in a complete description of the surface. The polynomials ($Z_i$) used are the normalized Zernike polynomials.

$$z(\rho, \theta) = \sum_{i=1}^{L} a_i Z_i \tag{1b}$$

These polynomials are special because they are orthonormal over a continuous unit circle. They are commonly used to describe wavefront aberrations in the field of optics. Corneal topographers measure the elevation heights at a discrete number of points. The Zernike polynomials are not orthogonal over a discrete set of points. However, applying an orthogonalization procedure, termed Gram-Schmidt orthogonalization, to the height data, allows the data to be fit in terms of Zernike polynomials maintaining the advantages of an orthogonal fit. Sixty-six coefficients (a's) were used to fit the height data provided by the Orbscan® software. A Matlab™ algorithm was used in the fitting procedure. The radius and asphericity value can be approximated from the Zernike coefficients (Equations 2b and 3b) and the conic constant of the surface is simply $K^2-1$ (from this we know that for a sphere $K^2=1$). The fitting procedure is well described in a number of references. Four different articles are refereed to here: "Wavefront fitting with discrete orthogonal polynomials in a unit radius circle", Daniel Malacara, Optical Engineering, June 1990, Vol. 29 No. 6, "Representation of videokeratoscopic height data with Zernike polynomials", J. Schwiegerling, J. Greivenkamp and J. Miller, JOSA A, October 1995, Vol. 12 No. 10, "Wavefront interpretation with Zernike polynomials" J. W. Wang and D. E. Silva, Applied Optics, May 1980, Vol. 19, No. 9 and "Corneal wave aberration from videokeratography: accuracy and limitations of the procedure", Antonio Guirao and Pablo Artal, J Opt Soc Am A Opt Image Sci Vis June 2000, Vol. 17(6):955-65.

$$R = \frac{r_{pupil}^2}{2(2\sqrt{3}\, a_4 - 6\sqrt{5}\, a_{11})} \tag{2b}$$

$$K_{sq} = \frac{8R^3}{r_o^4} 6\sqrt{5}\, a_{11} \tag{3b}$$

Calculation of Wavefront Aberration:

Knowing the shape of the anterior corneal surface (Zernike coefficients described above as a's), it is possible to determine the wavefront aberration contributed by this surface using a raytrace procedure. This is described in for example "Corneal wave aberration from videokeratography: accuracy and limitations of the procedure", Antonio Guirao and Pablo Artal, J Opt Soc Am A Opt Image Sci Vis June 2000, Vol. 17(6):955-65.

Figure 12:
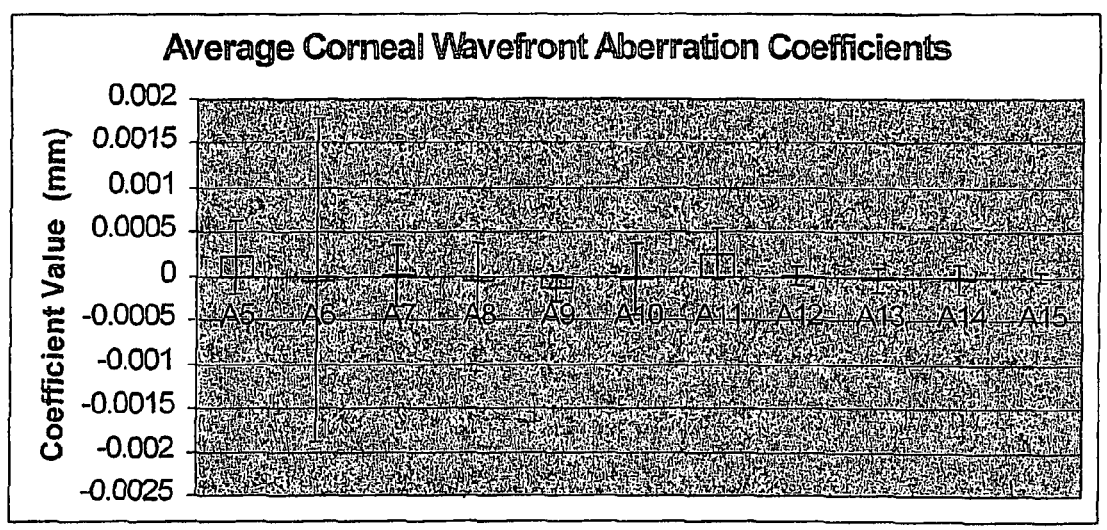
FIG. 12 shows average corneal wavefront aberration coefficients.

Results:

Average Corneal Spherical Aberration and Shape:

The 71 subjects were evaluated using the criteria described above for a 6 mm aperture. The wavefront aberration of each subject was determined after fitting the surface elevation with Zernike polynomials. FIG. 12 shows that average and standard deviation of each Zernike term (normalized format). The error bars represent ±1 standard deviation. There are three aberrations that are significantly different from zero on average in our population. These are astigmatism (A5), coma (A9) and spherical aberration (A11). Spherical aberration is the only rotationally symmetric aberration, making it the only aberration that can be corrected with a rotationally symmetric IOL.

Figure 13:
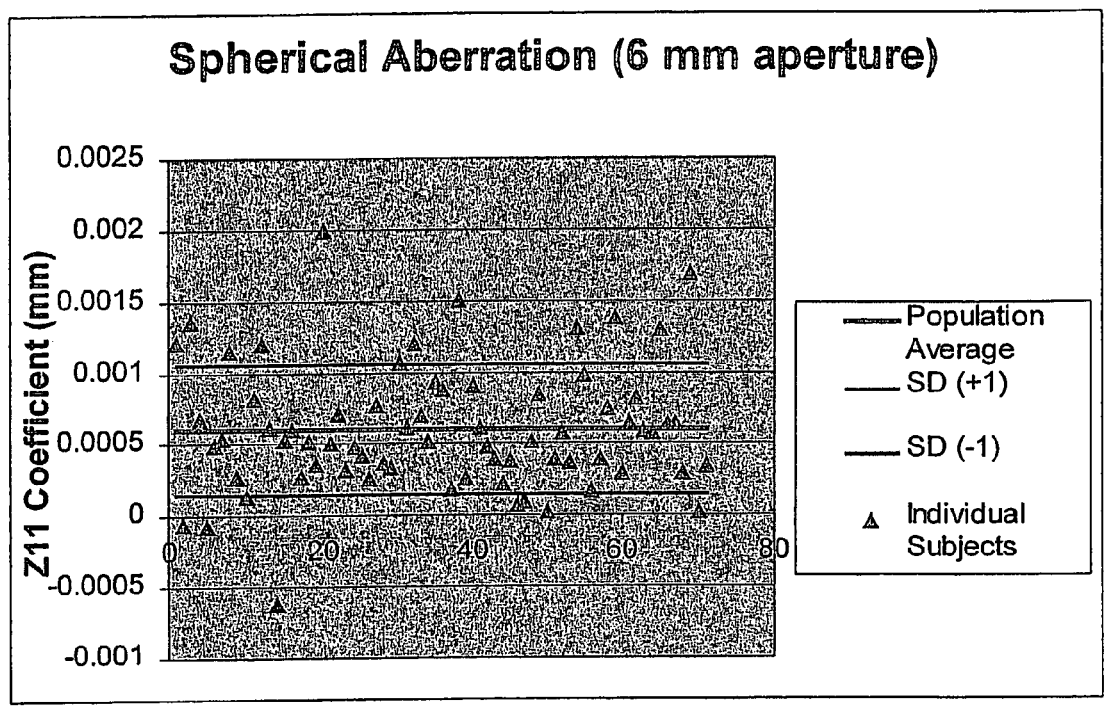
FIG. 13 shows a scatter plot of the spherical aberration of 71 subjects for a 6 mm diameter aperture.

FIG. 13 shows a scatter plot of the value of the Zernike coefficient (OSLO format) representing spherical aberration for each of the 71 subjects before cataract surgery. The solid line in the middle represents the average spherical aberration, while the dotted lines represent +1 and −1 standard deviation. Table 8 lists the average, standard deviation, maximum and minimum values for the radius, aspheric constant, spherical aberration and root mean square error.

TABLE 8 the average, standard deviation, maximum and minimum values for the radius, aspheric constant, spherical aberration and root mean square error for a 6 mm aperture.

|  | Average Value | Standard Deviation | Maximum | Minimum |
|---|---|---|---|---|
| R (mm) | 7.575 | 0.333 | 8.710 | 7.072 |
| Ksq | 0.927 | 0.407 | 2.563 | 0.0152 |
| SA coefficient OSLO format (in mm) | 0.000604 | 0.000448 | 0.002003 | −0.000616 |
| RMSE | 0.000055 | 0.00000482 | 0.000069 | 0.000045 |

Figure 14:
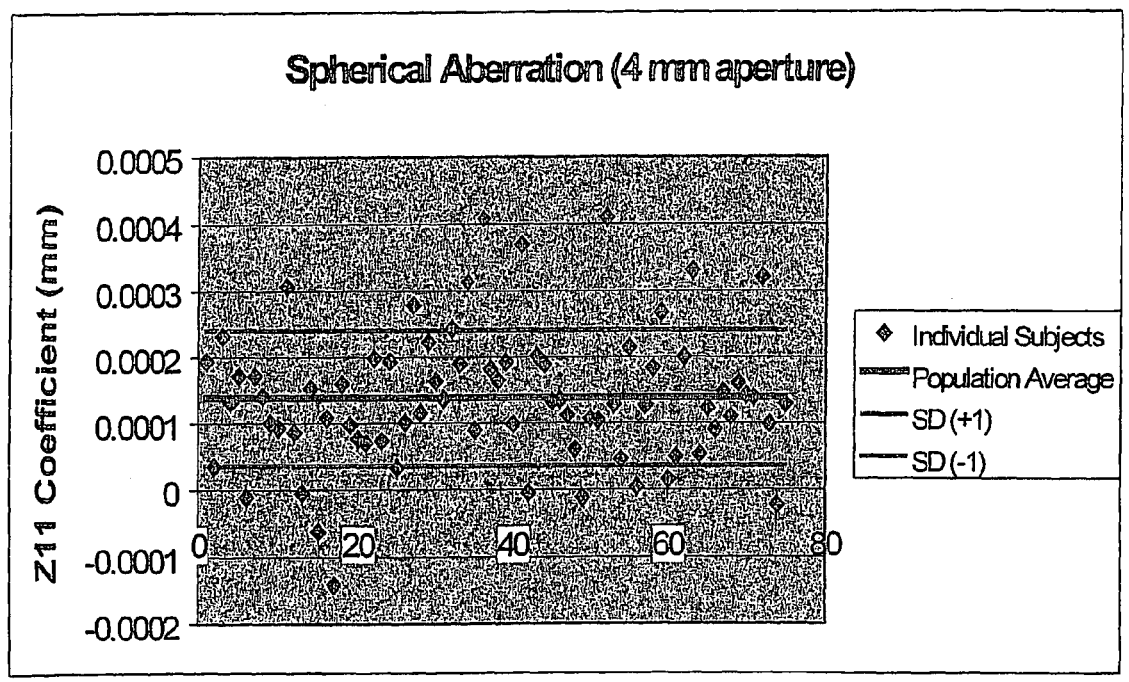
FIG. 14 shows a scatter plot of the spherical aberration of 71 subjects for a 4 mm diameter aperture.
Figure 15:
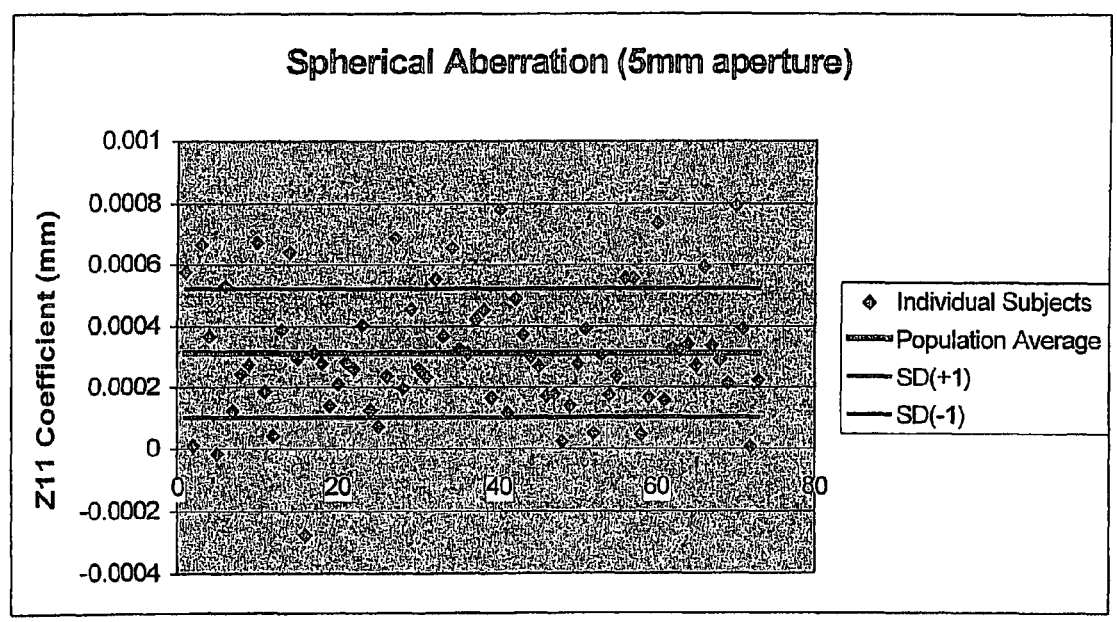
FIG. 15 shows a scatter plot of the spherical aberration of 71 subjects for a 5 mm diameter aperture.
Figure 16:
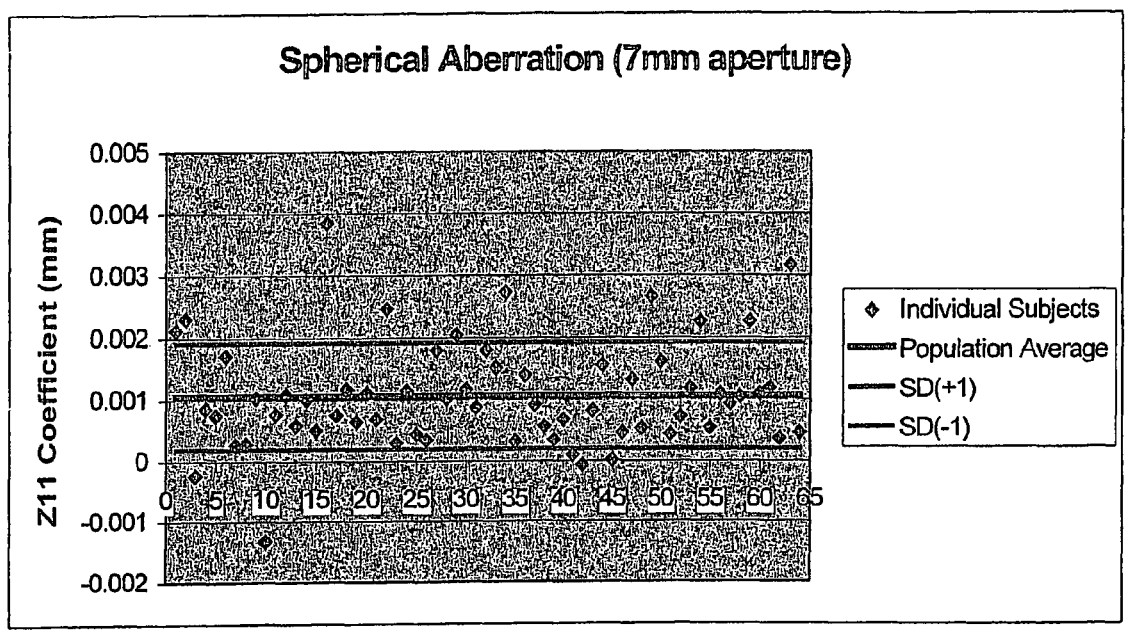
FIG. 16 shows a scatter plot of the spherical aberration of 71 subjects for a 7 mm diameter aperture.

Tables 9, 10 and 11 below show the corresponding results for aperture sizes of 4, 5 and 7 mm respectively. FIGS. 14, 15 and 16 are the corresponding scatter plots.

TABLE 9

The average, standard deviation, maximum and minimum values for the radius, aspheric constant, spherical aberration and root mean square error using an aperture diameter of 4 mm.

|  | Average Value | Standard Deviation | Maximum | Minimum |
|---|---|---|---|---|
| R | 7.56292 | 0.320526 | 8.688542 | 7.067694 |
| Ksq | 0.988208 | 0.437429 | 2.33501 | −0.051091 |
| SA (A11 in mm) | 0.000139 | 0.000103 | 0.00041 | −0.000141 |
| RMSE | 4.52E−05 | 4E−06 | 0.000054 | 0.000036 |

TABLE 10

The average, standard deviation, maximum and minimum values for the radius, aspheric constant, spherical aberration and root mean square error using an aperture diameter of 5 mm.

|  | Average Value | Standard Deviation | Maximum | Minimum |
|---|---|---|---|---|
| R | 7.55263 | 0.320447 | 8.714704 | 7.09099 |
| Ksq | 0.945693 | 0.364066 | 2.045412 | 0.044609 |
| SA (A11 in mm) | 0.00031189 | 0.000208 | 0.000793 | −0.000276 |
| RMSE | 4.7E−05 | 4.02E−06 | 0.000057 | 0.000037 |

TABLE 11

The average, standard deviation, maximum and minimum values for the radius, aspheric constant, spherical aberration and root mean square error using an aperture diameter of 7 mm.

|  | Average Value | Standard Deviation | Maximum | Minimum |
|---|---|---|---|---|
| R | 7.550226 | 0.336632 | 8.679712 | 7.040997 |
| Ksq | 0.898344 | 0.416806 | 2.655164 | −0.04731 |
| SA (A11 in mm) | 0.001058 | 0.000864 | 0.003847 | −0.001319 |
| RMSE | 7.58E−05 | 1.02E−05 | 0.000112 | 0.000057 |

Design Cornea:

One model cornea was designed and each Z11 lens power was designed using this cornea. The cornea was designed so that it had a spherical aberration that is the same as the average calculated for the population. The design cornea radii and aspheric constants are listed in Table 12 for different aperture sizes. In every case, the radius of curvature was taken to be the average radius determined from the Zernike fit data. The aspheric constant was varied until the spherical aberration value of the model cornea was equal to the average spherical aberration value for the population.

TABLE 12

The design cornea radii and aspheric constants for aperture diameters of 4, 5, 6, and 7 mm.

| Aperture size (mm) | Radius (mm) | Conic Constant (OSLO value, $K^2 - 1$) | Z11 Coefficient (mm) |
|---|---|---|---|
| 4 | 7.563 | −0.0505 | 0.000139 |
| 5 | 7.553 | −0.1034 | 0.000312 |
| 6 | 7.575 | −0.14135 | 0.000604 |
| 7 | 7.55 | −0.1810 | 0.001058 |

As discussed previously, the 6 mm aperture diameter values are used for the design cornea. This choice enables us to design the Z11 lens so that it has no spherical aberration (when measured in a system with this cornea) over a 5.1 mm lens diameter. The OSLO surface listing for the Z11 design cornea is listed in Table 13. The refractive index of the cornea is the keratometry index of 1.3375.

These values were calculated for a model cornea having a single surface with a refractive index of the cornea of 1.3375. It is possible to use optically equivalent model formats of the cornea without departing from the scope of the invention. For example multiple surface corneas or corneas with different refractive indices could be used.

TABLE 13

OSLO surface listing for the Z11 design cornea.

| Surface # | Radius (mm) | Thickness (mm) | Aperture Radius (mm) | Conic Constant (cc) | Refractive index |
|---|---|---|---|---|---|
| Object | — | 1.0000e+20 | 1.0000e+14 | — | 1.0 |
| 1 (cornea) | 7.575000 | 3.600000 | 3.000000 | −0.141350 | 1.3375 |
| 2 (pupil) | — | — | 2.640233 | — | 1.3375 |
| 3 | — | 0.900000 | 2.64023 | — | 1.3375 |
| 4 | — | 25.519444 | 2.550292 | — | 1.3375 |
| 5 | — | — | 2.2444e−05 | — | 1.3375 |

Lens Design:

Each Z11 lens was designed to balance the spherical aberration of the design cornea. The starting point for design was the CeeOn Edge© 911 lens described in U.S. Pat. No. 5,444,106 of the same power, with modified edge and center thickness. The lens was then placed 4.5 mm from the anterior corneal surface. The distance from the anterior corneal surface is not that critical and could be varied within reasonable limits. The surface information for the starting point eye model for the 22 D lens design process is listed in Table 14. The anterior surface of the lens was described using the formula shown in Equation 4. The variables cc, ad and ae were modified to minimize the spherical aberration. The variables are determined for an aperture size of 5.1 mm and the surface is extrapolated from these values to the optical aperture size of 6 mm. The resulting 22D Z11 eye model is listed in Table 15. The anterior surface of this 22D lens has been modified in such a way that the spherical aberration of the system (cornea+lens) is now approximately equal to 0. The wavefront aberration coefficients as calculated by OSLO for the CeeOn Edge 911 22D lens eye model and the 22D Z11 lens eye model are listed below in Table 16. Note that the coefficient representing spherical aberration for the starting point eye model is 0.001005 mm for a 6 mm diameter aperture placed at the cornea, while the same coefficient for the eye model with the designed Z11 lens is −1.3399e-06 mm. The same process as described above for a 22D lens can similarly be performed for any other lens power.

$$z = \frac{(1/R)r^2}{1 + \sqrt{1 - \left(\frac{1}{R}\right)^2 (cc+1)r^2}} + adr^4 + aer^6 \quad (4)$$

TABLE 14

Surface data for the starting point averaged eye model and a 22D lens

| Surface # | Radius (mm) | Thickness (mm) | Aperture Radius (mm) | Conic Constant (cc) | Refractive index |
|---|---|---|---|---|---|
| Object | — | 1.0000e+20 | 1.0000e+14 | — | 1.0 |
| 1 (cornea) | 7.575 | 3.600000 | 3.000003 | −0.14135 | 1.3375 |
| 2 (pupil) | — | — | 2.640233 | — | 1.336 |
| 3 | — | 0.900000 | 2.64023 | — | 1.336 |
| 4 (lens) | 11.043 | 1.164 | 2.550191 | — | 1.458 |
| 5 (lens) | −11.043 | 17.1512 | 2.420989 | — | 1.336 |
| 6 (image) | 0.0 | −0.417847 | 0.058997 | — | — |

TABLE 15

Surface data for the averaged eye model and the final 22D Z11 lens

| Surface # | Radius (mm) | Thickness (mm) | Aperture Radius (mm) | Conic Constant (cc) | 4th Order aspheric Constant | 6th Order aspheric constant | Refractive index |
|---|---|---|---|---|---|---|---|
| Object | — | 1.0e+20 | 1.00e+14 | — | | | 1.0 |
| 1 (cornea) | 7.575 | 3.60 | 3.00 | −0.14135 | | | 1.3375 |
| 2 (pupil) | — | — | 2.64 | — | | | 1.336 |
| 3 | — | 0.90 | 2.64 | — | | | 1.336 |
| 4 (lens) | 11.043 | 1.164 | 2.55 | −1.03613 | −0.000944 | −1.37e-05 | 1.458 |
| 5 (lens) | −11.043 | 17.1512 | 2.42 | — | | | 1.336 |
| 6 (image) | — | — | 1.59e-05 | — | — | — | — |

TABLE 16

Zernike coefficients (OSLO format) for the average cornea and a 22D 911 lens and the average cornea and the 22D Z11 lens

| Coefficient | Average cornea + 22D 911 | Average cornea + 22D Z11 |
|---|---|---|
| a1 | −0.000962 | −1.896e-06 |
| a2 | 0.0 | 0.0 |
| a3 | 0.0 | 0.0 |
| a4 | 2.3101e-05 | −3.9504e-06 |
| a5 | 0.0 | 0.0 |
| a6 | 0.0 | 0.0 |
| a7 | 0.0 | 0.0 |
| a8 | 0.0 | 0.0 |
| a9 | 0.00105 | −1.3399e-06 |
| a10 | 0.0 | 0.0 |
| a11 | 0.0 | 0.0 |
| a12 | 0.0 | 0.0 |
| a13 | 0.0 | 0.0 |
| a14 | 0.0 | 0.0 |
| a15 | 0.0 | 0.0 |

The optical form chosen for the new Z11 design is an equiconvex lens made from a silicone with refractive index of 1.458. The spherical aberration of an average cornea is balanced by the Z11 lens yielding a system without spherical aberration. The front surface of the lens is modified such that the optical path lengths of all on-axis rays within the design aperture are the same producing a point focus. This feature can be achieved with many lens forms. The Z11 lens could therefore be designed on a convex-plano, plano-convex, non-equiconvex lens or any other design yielding a positive lens. The Z11 concept could also be extended in order to encompass a negative lens used to correct the refractive errors of the eye. The front surface or back surface could also be modified to produce the needed change in optical path difference that neutralizes the spherical aberration. There are therefore many possible designs that would achieve the goals of the Z11 lens design.

What is claimed:

1. A method of providing an intraocular lens for implantation into an eye, comprising:
    measuring at least one surface of a cornea;
    based on the measurement, determining a spherical aberration and an additional aberration; and
    based on the spherical aberration and the additional aberration, specifying an intraocular lens including an anterior surface and an opposing posterior surface;
    wherein at least one of the surfaces of the intraocular lens is characterized by an equation including a first coefficient configured to reduce a positive spherical aberration of a wavefront passing through the intraocular lens and at least one of the surfaces is characterized by an equation including a second coefficient configured to reduce an additional aberration of the wavefront.

2. The method of claim 1, wherein the additional aberration of the cornea is an astigmatism of the cornea.

3. The method of claim 1, wherein the first coefficient is a conical constant.

4. The method of claim 3, wherein the equation containing the first coefficient also contains coefficients for higher order variables of a radius from a center of the intraocular lens.

5. The method of claim 1, wherein the second coefficient is a coefficient representing astigmatism in a Zernike polynomial.

6. The method of claim 1, wherein specifying comprises selecting an intraocular lens from a kit comprising lenses with a suitable power range and within each power range a plurality of lenses having different aberrations.

7. The method of claim 1, wherein specifying comprises providing a model of an intraocular lens, determining a value for the first coefficient to reduce a positive spherical aberration of a wavefront passing through the model intraocular lens, determining a value for the second coefficient to reduce an astigmatism a wavefront passing through the model intraocular lens, and based on the first and second coefficients, providing the intraocular lens for implantation into an eye.

8. The method of claim 7, wherein the intraocular lens is an individually tailored lens.

9. The method of claim 7, wherein the intraocular lens is selected from a kit comprising lenses with a suitable power range and within each power range a plurality of lenses having different aberrations.

10. The method of claim 1, wherein one of the surfaces is characterized both by the equation including the first coefficient and the equation including the second coefficient.

11. The method of claim 1, wherein one of the anterior surface and the posterior surface is characterized by the equation including the first coefficient, and the other of the anterior surface and the posterior surface is characterized by the equation including the first coefficient.

12. The method of claim 1, wherein the wavefront is characterized by Zernike coefficients of a Zernike polynomial representing a wavefront and the intraocular lens is configured to reduce Zernike coefficients referring to spherical aberration and astigmatism terms.

13. The method of claim 1, wherein the wavefront is characterized by Zernike coefficients of a Zernike polynomial representing a wavefront and the intraocular lens is configured to reduce Zernike a coefficient referring to spherical aberration term or an astigmatism term.

14. The method of claim 1, wherein the wavefront is from light passing through a cornea.

15. The method of claim 1, wherein the cornea is the cornea on an individual.

16. The method of claim 1, wherein the cornea is a model cornea.

17. The method of claim 16, wherein the model cornea is based on a population and has an average spherical aberration value for the population.

18. The method of claim 16, wherein the model cornea is based on a population and has an average astigmatism value for the population.

19. The method of claim 16, wherein the spherical aberration is an average corneal spherical aberration of a population.

20. The method of claim 19, wherein the model cornea is produced by measuring the corneas of the population.

21. The method of claim 19, wherein the population includes people of a specific age group, people with a cataract, people who have received a corneal ablative procedure, people who are candidates for a corneal ablative procedure, or people who are highly myopic or highly hyperopic.

22. The method of claim 1, wherein the spherical aberration and the additional aberration are aberrations of the cornea.

23. The method of claim 1, wherein the spherical aberration and the additional aberration are aberrations of an optical system including the cornea and the intraocular lens.

24. The method of claim 1, further comprising performing a wavefront analysis of an aphakic eye.

25. An intraocular lens, comprising:
an anterior surface and an opposing posterior surface;
wherein at least one of the surfaces of the intraocular lens is characterized by an equation including a first coefficient configured to reduce a positive spherical aberration of a wavefront passing through the intraocular lens and at least one of the surfaces is characterized by an equation including a second coefficient configured to reduce an additional aberration of the wavefront.

26. The intraocular lens of claim 25, wherein the additional aberration of the cornea is an astigmatism of the cornea.

27. The intraocular lens of claim 25, wherein the first coefficient is a conical constant.

28. The intraocular lens of 27, wherein the equation containing the first coefficient also contains coefficients for higher order variables of a radius from a center of the intraocular lens.

29. The intraocular lens of claim 25, wherein the second coefficient is a coefficient representing astigmatism in a Zernike polynomial.

30. The intraocular lens of claim 25, wherein the intraocular lens is from a kit comprising lenses with a suitable power range and within each power range a plurality of lenses having different aberrations.

31. The intraocular lens of claim 25, wherein one of the surfaces is characterized both by the equation including the first coefficient and the equation including the second coefficient.

32. The intraocular lens of claim 25, wherein one of the anterior surface and the posterior surface is characterized by the equation including the first coefficient, and the other of the anterior surface and the posterior surface is characterized by the equation including the first coefficient.

33. The intraocular lens of claim 25, wherein the wavefront is characterized by Zernike coefficients of a Zernike polynomial representing a wavefront and the intraocular lens is configured to reduce Zernike coefficients referring to spherical aberration and astigmatism terms.

34. The intraocular lens of claim 25, wherein the spherical aberration is an average corneal spherical aberration of a population.

35. The intraocular lens of claim 34, wherein the population includes people of a specific age group, people with a cataract, people who have received a corneal ablative procedure, people who are candidates for a corneal ablative procedure, or people who are highly myopic or highly hyperopic.

36. The intraocular lens of claim 25, wherein the wavefront is characterized in terms of polynomials and the intraocular lens is configured to reduce the spherical aberration and additional aberration as expressed by polynomials.

37. The intraocular lens of claim 25, wherein the wavefront is characterized by Zernike coefficients of a Zernike polynomial representing a wavefront and the intraocular lens is configured to reduce Zernike coefficients referring to spherical aberration and an additional aberration up to the fourth order.

38. The intraocular lens of claim 25, wherein the wavefront is characterized by Zernike coefficients of a Zernike polynomial representing a wavefront and the intraocular lens is configured to reduce Zernike coefficients referring to spherical aberration and an additional aberration above the fourth order.

39. The intraocular lens of claim 25, wherein the lens has at least one nonspherical surface capable of transferring a wavefront having passed through the cornea of the eye into a substantially spherical wavefront having its center in the retina of the eye.

40. The intraocular lens of claim 39, wherein the wavefront is substantially spherical with respect to aberration terms expressed in rotationally symmetric Zernike terms up to the fourth order.

41. The intraocular lens of claim 25 wherein the $11^{th}$ Zernike coefficient of a wavefront from an optical system comprising a cornea and the intraocular lens is brought sufficiently close to zero such that the eye is sufficiently free from spherical aberration.

42. The intraocular lens of claim 25, wherein the intraocular lens balances the spherical aberration of a cornea that has a Zernike polynomial coefficient representing spherical aberration of the wavefront aberration with a value in the interval from 0.000156 mm to 0.001948 mm for a 3 mm aperture radius using polynomials expressed in OSLO format.

43. The intraocular lens of claim 25, wherein the intraocular lens balances the spherical aberration of a cornea that has a Zernike polynomial coefficient representing spherical aberration of the wavefront aberration with a value in the interval from 0.000036 mm to 0.000448 mm for a 2 mm aperture radius using polynomials expressed in OSLO format.

44. The intraocular lens of claim 25, wherein the intraocular lens balances the spherical aberration of a cornea that has a Zernike polynomial coefficient representing spherical aberration of the wavefront aberration with a value in the interval from 0.0001039 mm to 0.0009359 mm for a 2.5 mm aperture radius using polynomials expressed in OSLO format.

45. The intraocular lens of claim 25, wherein the intraocular lens balances the spherical aberration of a cornea that has a Zernike polynomial coefficient representing spherical aberration of the wavefront aberration with a value in the interval from 0.000194 mm to 0.00365 mm for a 3.5 mm aperture radius using polynomials expressed in OSLO format.

* * * * *

UNITED STATES PATENT AND TRADEMARK OFFICE
CERTIFICATE OF CORRECTION

PATENT NO. : 7,841,720 B2
APPLICATION NO. : 12/175395
DATED : November 30, 2010
INVENTOR(S) : Sverker Norrby et al.

Page 1 of 1

It is certified that error appears in the above-identified patent and that said Letters Patent is hereby corrected as shown below:

On the Title page of the Patent, Related U.S. Application Data, Item (60) should read as follows:

(60) Continuation of application No. 11/619,098, filed on Jan. 2, 2007, now abandoned, which is a division of application No. 10/606,910, filed on Jun. 26, 2003, now Pat. No. 7,241,311, which is a division of application No. 09/863,546, filed on May 23, 2001, now Pat. No. 6,609,793, which claims benefit of 60/207,734 filed May 26, 2000, and claims benefit of 60/259,924 filed January 5, 2001.

In the Specifications:

In column 1, line 7, under Related Applications, the paragraph should read as follows:

The present application is a continuation application of U.S. Ser. No. 11/619,098, filed Jan. 2, 2007, which is a divisional application of U.S. Ser. No. 10/606,910, filed Jun. 26, 2003, now U.S. Pat. No. 7,241,311, issued Jul. 10, 2007, which is a divisional application of U.S. Ser. No. 09/863,546, filed May 23, 2001, now U.S. Pat. No. 6,609,793, issued Aug. 26, 2003, which claims benefit of 60/207,734 filed May 26, 2000, and claims benefit of 60/259,924 filed January 5, 2001.

Signed and Sealed this
Sixteenth Day of April, 2013

Teresa Stanek Rea
*Acting Director of the United States Patent and Trademark Office*